US010639361B2

(12) United States Patent
Marchand

(10) Patent No.: US 10,639,361 B2
(45) Date of Patent: May 5, 2020

(54) **METHOD FOR PREVENTING OR TREATING *M TUBERCULOSIS* INFECTION**

(71) Applicant: GLAXOSMITHKLINE BIOLOGICALS, S.A.

(72) Inventor: Martine Marchand, Rixensart (BE)

(73) Assignee: GLAXOSMITHKLINE BIOLOGICALS, S.A., Rixensart (BE)

( * ) Notice: Subject to any disclaimer, the term of this patent is extended or adjusted under 35 U.S.C. 154(b) by 0 days.

(21) Appl. No.: 16/451,040

(22) Filed: Jun. 25, 2019

(65) Prior Publication Data

US 2019/0307872 A1 Oct. 10, 2019

Related U.S. Application Data

(60) Division of application No. 16/135,553, filed on Sep. 19, 2018, now Pat. No. 10,350,283, which is a division of application No. 15/463,557, filed on Mar. 20, 2017, now Pat. No. 10,105,430, which is a continuation of application No. 14/603,935, filed on Jan. 23, 2015, now Pat. No. 9,655,958, which is a continuation of application No. 13/895,574, filed on May 16, 2013, now Pat. No. 9,056,913, which is a continuation of application No. 11/912,730, filed as application No. PCT/EP2006/004319 on Apr. 27, 2006, now Pat. No. 8,470,338.

(60) Provisional application No. 60/777,017, filed on Feb. 27, 2006, provisional application No. 60/676,549, filed on Apr. 29, 2005.

(51) Int. Cl.
| | |
|---|---|
| *A61K 39/00* | (2006.01) |
| *A61K 39/02* | (2006.01) |
| *A61K 39/04* | (2006.01) |
| *C07K 14/35* | (2006.01) |
| *A61K 31/4409* | (2006.01) |
| *A61K 31/496* | (2006.01) |

(52) U.S. Cl.
CPC .......... *A61K 39/04* (2013.01); *A61K 31/4409* (2013.01); *A61K 31/496* (2013.01); *C07K 14/35* (2013.01); *A61K 2039/523* (2013.01); *A61K 2039/53* (2013.01); *A61K 2039/55566* (2013.01); *A61K 2039/55572* (2013.01); *A61K 2039/55577* (2013.01); *A61K 2039/575* (2013.01)

(58) Field of Classification Search
CPC ......... A61K 39/00; A61K 39/04; C07H 21/02
USPC .................... 424/184.1, 185.1, 234.1, 248.1; 536/23.1, 23.5
See application file for complete search history.

(56) References Cited

U.S. PATENT DOCUMENTS

| | | | |
|---|---|---|---|
| 5,284,933 | A | 2/1994 | Dobeli et al. |
| 9,352,030 | B2 | 5/2016 | Godart et al. |
| 2013/0280289 | A1 | 10/2013 | Godart et al. |

FOREIGN PATENT DOCUMENTS

| | | |
|---|---|---|
| WO | 19960033739 | 10/1996 |
| WO | 19970009428 | 3/1997 |
| WO | 19970009429 | 3/1997 |
| WO | 19990051748 | 10/1999 |
| WO | 20010024820 A1 | 4/2001 |
| WO | 20010098460 A2 | 12/2001 |
| WO | 2002/072792 A2 | 9/2002 |
| WO | 20030070187 A2 | 4/2003 |
| WO | 20100121618 A1 | 10/2010 |

OTHER PUBLICATIONS

Andersen, "Vaccine strategies against latent tuberculosis infection"; Trends in Microbiology; 2007; pp. 7-13; vol. 15, No. 1.
Demissie, et al., "Recognition of Stage-Specific Mycobacterial Antigens Differentiates between Acute and Latent Infections with *Mycobacterium tuberculosis*" Clinical and Vaccine Immunology; 2006; pp. 179-186; vol. 13, No. 2.
Hochuli, et al., "New Metal Chelate Adsorbent Selective for Proteins and Peptides Containing Neighbouring Histidine Residues." Journal of Chromatography; 1987; pp. 177-184; vol. 411.
Hochuli, et al., "Genetic Approach to Facilitate Purification of Recombinant Proteins with a Novel Metal Chelate Adsorbent." Bio/Technology; 1988; p. 1321-1325.
Lewinsohn, et al., "Human Dendritic Cells Presenting Adenovirally Expressed Antigen Elicit *Mycobacterium tuberculosis*-Specific CD8+ T Cells." American Journal of Respiratory and Critical Care Medicine; 2002; pp. 843-848.
Paramasivan, et al., "Bactericidal Action of Gatifloxacin, Rifampin, and Isoniazid on Logartithmic- and Stationary-Phase Cultures of *Mycobacterium tuberculosis*." Antimicrobial Agents and Chemotherapy; 2005; pp. 627-631; vol. 49, No. 2.
Xie, et al., "Differential Antibiotic Susceptibilities of Starved *Mycobacterium tuberculosis* Isolates." Antimicrobial Agents and Chemotherapy; 2005; pp. 4 778-4 780; vol. 49, No. 11.

(Continued)

*Primary Examiner* — Rodney P Swartz

(57) ABSTRACT

The present invention is directed to methods of preventing reactivation of active and latent *M. tuberculosis* infections by administering a pharmaceutical composition comprising a nucleic acid encoding a Mtb72f fusion protein, or a Mtb72f fusion protein or an immunogenic fragment thereof, for example together with an adjuvant. The Mtb72f nucleic acid or fusion protein can be administered with one or more chemotherapeutic agents effective against a *M. tuberculosis* infection. The methods also provide for shortening the time course of a chemotherapeutic regimen against a *M. tuberculosis* infection.

10 Claims, 12 Drawing Sheets

Specification includes a Sequence Listing.

(56) References Cited

OTHER PUBLICATIONS

Al-Attiyah, et al., "In vitro Cellular Immune Responses to Complex and Newly Defined Recombinant Antigens of *Mycobacterium tuberculosis*", Clin. Exp. Immunol.,2004: 138: pp. 139-144.
Brandt, et al., "The protective effect of the *Mycobacterium bovis* BCG vaccine is increased by coadministration with the *Mycobacterium tuberculosis* 72-kilodalton fusion polyprotein Mtb72F in *M. tuberculosis*-infected guinea pigs," Infection and Immunity, 2004: 72(11) pp. 6622-6632.
Campuzano, et al., "The PGRS domain of *Mycobacterium tuberculosis* PE_PGRS Rv 1759c antigen is an effective subunit vaccine to prevent reactivation in a murine model of chronic tuberculosis", 2007: Vaccine, 25(18) pp. 3722-3729.
Cavusoglu, et al., "*Mycobacterium tuberculosis* infection and laboratory diagnosis in solid-organ transplant-recipients," Clinical Transplantation, 2002, 16(4) pp. 257-261.
Dillon. et al.. Molecular Characterization and Human T-Cell Responses to a Member of a Novel *Mycobacterium tuberculosis* mth39 Gene Family:, Infection and Immunity, 1999, 67 (6), pp. 2941-2950.
Irwin, et al., "Tracting antigen-specific CDS T Lymphocytes in the lungs of mice vaccinated with the Mtb72F polyprotein", Infection and Immunity, 2005, 73(9), pp. 5809-5816.
Lin, et al., "Understanding latent tuberculosis A moving target", A Journal of Immunology, The American Association of Immunologists Inc., Bethesda, MD, 2010, 185, pp. 15-22.
Lin et al., "Modeling patogen and host: in vitro, in vivo and in silco models of latent *Mycobacterium tuberclosis* infection", Drug Discovery Today: Disease Models, Elsevier Ltd., 2005, 2(2), pp. 149-154.
Lowrie, et al., "Therapy of Tuberculosis in Mice by DNA Vaccination" Nature, 1999, 400, pp. 269-271.
Moniruzzaman, et al., "A population based study of tuberculosis recurrence: Relapse Versus Reinfection", D18 Applying Edidemologic Findings to Improve Tuberculosis Control, Mini Symposium, Am J Respir Crit Care Med, May 19, 2010, 181,A5377.
Moreira, et al., "Mycobacterial Antigens Exacerbate Disease Manifestations in *Mycobacterium tuberculosis*-Infected Mice", Infection and Immunity, Apr. 2002, 70(4), pp. 2100-2107.
Reece, et al., "Skin Test Performed with Highly Purified *Mycobacterium tuberculosis* Recombinant Protein Triggers Tuberculin Shock in Infected Guinea Pigs", Infection and Immunity, American Society for Microbiology, 2005, 73(6), pp. 3301-3306.
Reed, et al., "Defined Tuberculosis Vaccine, Mtb72F/AS02A, Evidence of Protection in Cynomolgus Monkeys", PNAS US, 2009, 106(7), pp. 2301-2306.
Reed et al., "Tuberculosis Vaccine Development: from Mouse to man", Microbes and Infection, 2005, 7(5-6), pp. 922-931.
Repique et al., "DNA Immunization in a Mouse Model of Latent Tuberculosis: Effect of DNA Vaccination on Reactivation of Disease on Reinfection with a Secondary Challenge", Infection and Immunity, 2002, 70(7), pp. 3318-3323.
Scanga, at al., "Reactivation of Latent Tuberculosis: Variations on the Cornell Murine Model", Infection and Immunity, 1999, 67(9), pp. 4531-4538.

Shi, et al., "A review of Murine Models of Latent Tuberculosis Infection", Scandinavian Journal of Infection Diseases, Informa Healthcare, 2011, 42: pp. 848-856.
Skeiky, et al., "Cloning, Expression and Immunological Evaluation of Two Putative Secreted Serine Protease Antigens of *Mycobacterium tuberculosis*", Infection and Immunity, 1999, 67(8), pp. 3998-4007.
Skeiky, et al.,"Differential Immune Responses and Protective Efficacy Induced by Components of a Tuberculosis Polyprotein vaccine, Mtb72F, delivered as maked DNA or recombinant protein, Journal of Immunology", 2004, 172(12), pp. 7618-7628.
Tomioka, et al., "Anti-*Mycobacterium tuberculosis* activitied of new ftouroquinolones in combination with other antituberculous drugs", The Journal of Infection, 2002, 44(3), pp. 160-165.
Tsenova, et al.,"Evaluation of the Mtb72F polyprotein Vaccine in a rabbit model of tuberculous medingitis", Infection and Immunity, 2006, 74(4), pp. 2392-2401.
Turner, et al., "Effective Preexposure Tuberculosis Vaccines Fail to Protect When they are given in an Immunotherapeutic Mode", Infection and Immunity, Mar. 2000, 68(3), pp. 1706-1709.
Vekemans, et al., "Immune Responses to Mycobacterial Antigens in the Gambian Population: Implications for Vaccines and Immunodiagnostic Test Design", Infection and Immunity, 2004, 72(1 ), pp. 381-388.
Von Eschen, et al., "The Candidate Tuberculosis Vaccine Mtb72F/AS02A" Human Vaccines, 2009, 5(7), pp. 475-482.
Wayne, et al., "Dormancy if *Mycobacterium tuberculosis* and Latency of Disease" European Journal of Clinical Microbiology and Infections Diseases, Tuberculosis Research Laboratory, Long Beach, CA, 1994, 13(11), pp. 908-914.
WHO 2009 update Tuberculosis Facts, WHO Stop TB Department.
Kruppa et al.. Coordinative Peptide Recognition, Makin Intermolecular Processes Intramolecular, Dissertation, (2005) pp. 1-254.
Cardona et al., Immunotherapy with fragmented *Mycobacterium tuberculosis* Cells Increases the Effectiveness of Chemotherapy against a Chronical Infection in a Murine Model of Tuberculosis, Vaccine, (2005), vol. 23, pp. 1393-1398.
Carosi, et al., Prophylaxis for Tuberculosis in Europe Ongoing Research, From the Clinic of Infections and Tropical Diseases, ( 1996) 22, pp. 855-860.
Terpe, et al., Overview of tag protein Fusions: From Molecular and Biochemical Fundamentals to Commercial Systems, (2002), vol. 60, No. 5., pp. 523-533.
Divorin et al., Elimination of Tuberculous Meningitis in Children, Sovetskaya Medistsina, (1958) vol. 22, No. 12., pp. 125-130.
Khan, et al., Histidine Affinity Tages Affect MSPI 42 Structural statbility and Immunodominance in Mice, (2012), vol. 7 pp. 133-147.
Krakowska, et al., The Course of Socalled Inactive Tuberculosis During a 5-Year Observation Period, (1966), vol. 34, No. 10, pp. 861-865.
Leroux-Roels, et al., Improced CD4+ T cell responses to *Mycobacterium tuberculosis* in PPD negative adults by M72/AS01 as compared to the M72/AS02 and Mtb72F/AS02 Tuberculosis Candidate Vaccine Formulations: A Randomized Trial; Vaccine, (2013) vol. 31, pp. 2196-2206.
Randolph, et al., The Two Faces of His Tag : Immune Response Versus Ease of Protein Purification, Biotechnology J., (2012), vol. 7, pp. 133-137.

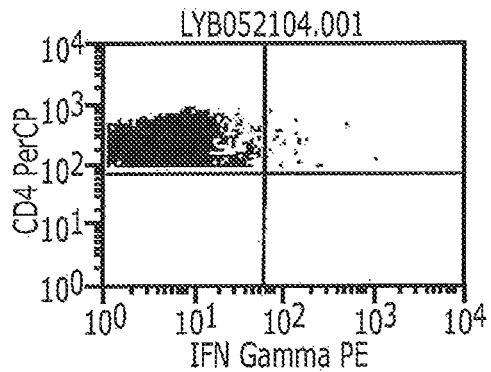

File: LYB052104.001
Sample ID: SWR 1 Media
Gate: CD4
Gated Events: 10129
Total Events: 236412

*Fig. 6A.1*

| Quad | Events | % Gated | % Total |
|---|---|---|---|
| UL | 10110 | 99.81 | 4.28 |
| UR | 19 | 0.19 | 0.01 |
| LL | 0 | 0.00 | 0.00 |
| LR | 0 | 0.00 | 0.00 |

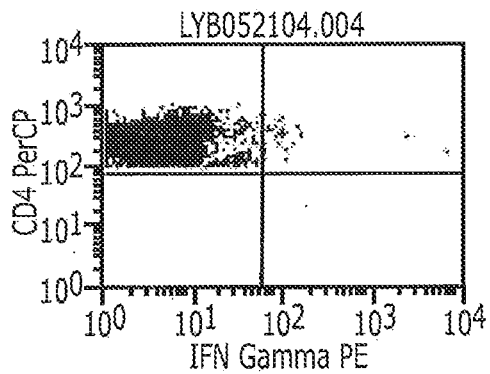

File: LYB052104.004
Sample ID: SWR 2 Media
Gate: CD4
Gated Events: 15138
Total Events: 184156

*Fig. 6A.2*

| Quad | Events | % Gated | % Total |
|---|---|---|---|
| UL | 15114 | 99.84 | 8.21 |
| UR | 24 | 0.16 | 0.01 |
| LL | 0 | 0.00 | 0.00 |
| LR | 0 | 0.00 | 0.00 |

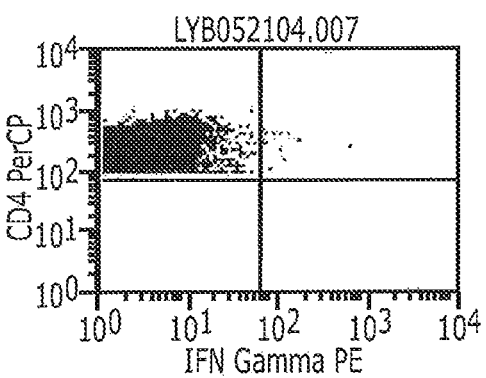

File: LYB052104.007
Sample ID: SWR 4 Media
Gate: CD4
Gated Events: 19494
Total Events: 180809

*Fig. 6A.3*

| Quad | Events | % Gated | % Total |
|---|---|---|---|
| UL | 19483 | 99.94 | 10.78 |
| UR | 11 | 0.06 | 0.01 |
| LL | 0 | 0.00 | 0.00 |
| LR | 0 | 0.00 | 0.00 |

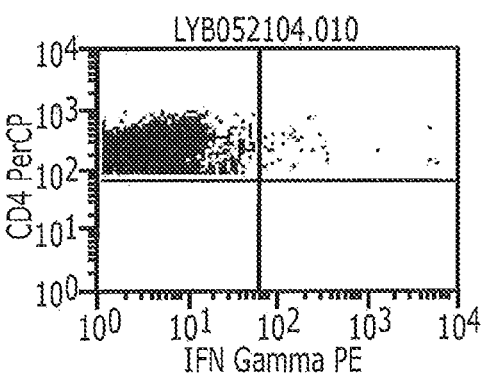

File: LYB052104.010
Sample ID: SWR 5 Media
Gate: CD4
Gated Events: 14295
Total Events: 193256

*Fig. 6A.4*

| Quad | Events | % Gated | % Total |
|---|---|---|---|
| UL | 14265 | 99.79 | 7.38 |
| UR | 30 | 0.21 | 0.02 |
| LL | 0 | 0.00 | 0.00 |
| LR | 0 | 0.00 | 0.00 |

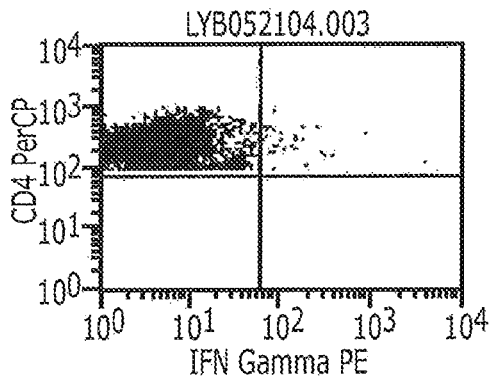

File: LYB052104.003
Sample ID: SWR 1 72F
Gate: CD4
Gated Events: 10257
Total Events: 232880

Fig. 6B.1

| Quad | Events | % Gated | % Total |
|---|---|---|---|
| UL | 10228 | 99.72 | 4.39 |
| UR | 29 | 0.28 | 0.01 |
| LL | 0 | 0.00 | 0.00 |
| LR | 0 | 0.00 | 0.00 |

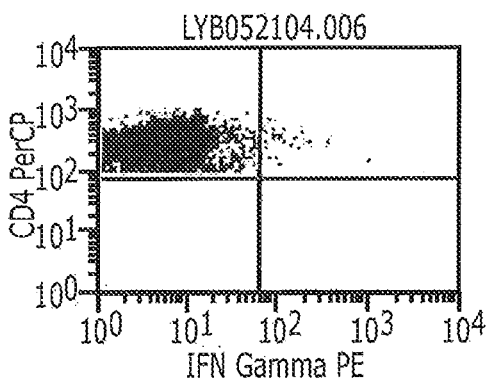

File: LYB052104.006
Sample ID: SWR 2 72F
Gate: CD4
Gated Events: 15634
Total Events: 190322

Fig. 6B.2

| Quad | Events | % Gated | % Total |
|---|---|---|---|
| UL | 15609 | 99.84 | 8.20 |
| UR | 25 | 0.16 | 0.01 |
| LL | 0 | 0.00 | 0.00 |
| LR | 0 | 0.00 | 0.00 |

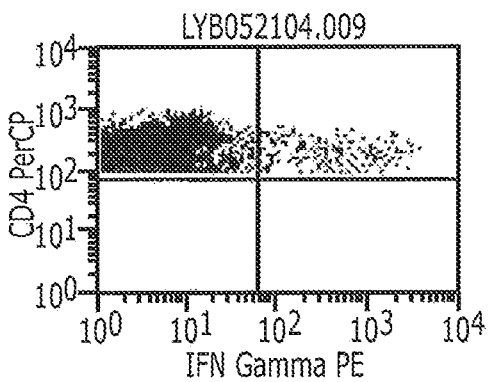

File: LYB052104.009
Sample ID: SWR 4 72F
Gate: CD4
Gated Events: 19555
Total Events: 186968

Fig. 6B.3

| Quad | Events | % Gated | % Total |
|---|---|---|---|
| UL | 19384 | 99.13 | 10.37 |
| UR | 171 | 0.87 | 0.09 |
| LL | 0 | 0.00 | 0.00 |
| LR | 0 | 0.00 | 0.00 |

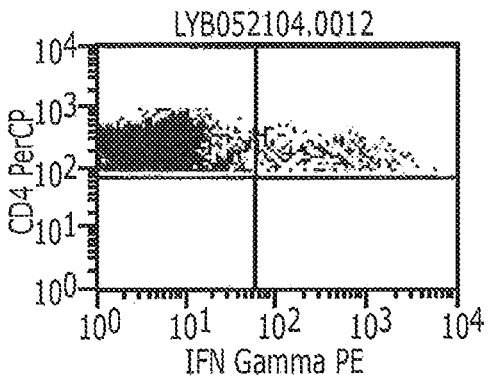

File: LYB052104.0012
Sample ID: SWR 5 72F
Gate: CD4
Gated Events: 14045
Total Events: 200028

Fig. 6B.4

| Quad | Events | % Gated | % Total |
|---|---|---|---|
| UL | 13849 | 98.60 | 6.92 |
| UR | 196 | 1.40 | 0.10 |
| LL | 0 | 0.00 | 0.00 |
| LR | 0 | 0.00 | 0.00 |

| Stims | Group 1 | | Group 2 | | Group 3 | | Group 4 | | Group 5 | |
|---|---|---|---|---|---|---|---|---|---|---|
| | Media | 72F | Media | 72F | Media | 72F | Media | 72F | Media | 72F |
| FNg+ % Gated | 0.19 | 0.28 | 0.16 | 0.16 | 0.31 | 0.8 | 0.06 | 0.87 | 0.21 | 1.4 |
| % Total | 0.01 | 0.01 | 0.01 | 0.01 | 0.04 | 0.1 | 0.01 | 0.09 | 0.02 | 0.1 |
| FMg+ % Gated | 1.78 | 1.55 | 0.45 | 0.56 | 0.42 | 2.87 | 0.22 | 0.59 | 0.22 | 0.61 |
| % Total | 0.05 | 0.04 | 0.02 | 0.03 | 0.03 | 0.18 | 0.01 | 0.05 | 0.01 | 0.06 |

METHOD FOR PREVENTING OR TREATING *M TUBERCULOSIS* INFECTION

CROSS-REFERENCE TO RELATED APPLICATIONS

This application is a divisional of U.S. patent application Ser. No. 16/135,553 is now U.S. Pat. No. 10,350,283, which is a divisional of U.S. patent application Ser. No. 15/463, 557, now U.S. Pat. No. 10,105,430 which is a continuation of U.S. patent application Ser. No. 14/603,935, now U.S. Pat. No. 9,655,958, which is a continuation of U.S. patent application Ser. No. 13/895,574, now U.S. Pat. No. 9,056, 913, which is a continuation of U.S. patent application Ser. No. 11/912,730, now U.S. Pat. No. 8,470,338, which is the US National Stage of International Application No. PCT/EP2006/004319, filed 27 Apr. 2006, which claims benefit of the filing date of U.S. Provisional Applications No. 60/777, 017, filed 27 Feb. 2006, and No. 60/676,549, filed 29 Apr. 2005, each of which are incorporated herein by reference.

FIELD OF THE INVENTION

The present invention relates to methods of preventing or treating reactivation of a *M. tuberculosis* infection in a mammal and to methods of shortening the time course of chemotherapy against a *M. tuberculosis* infection.

BACKGROUND OF THE INVENTION

Tuberculosis is a chronic infectious disease caused by infection with *M. tuberculosis* and other *Mycobacterium* species. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance. Even if a full course of treatment is completed, infection with *M. tuberculosis* is not eradicated from the infected individual but remains as a latent infection that can be reactivated.

In order to control the spread of tuberculosis, effective vaccination and accurate early diagnosis of the disease are of utmost importance. Currently, vaccination with live bacteria is the most efficient method for inducing protective immunity. The most common *mycobacterium* employed for this purpose is *Bacillus* Calmette-Guerin (BCG), an avirulent strain of *M. bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48-72 hours after injection, which indicates exposure to mycobacterial antigens. Sensitivity and specificity have, however, been a problem with this test, and individuals vaccinated with BCG cannot be distinguished from infected individuals.

While macrophages have been shown to act as the principal effectors of *Mycobacterium* immunity, T cells are the predominant inducers of such immunity. The essential role of T cells in protection against *Mycobacterium* infection is illustrated by the frequent occurrence of *Mycobacterium* infection in AIDS patients, due to the depletion of $CD4^+$ T cells associated with human immunodeficiency virus (HIV) infection. *Mycobacterium*-reactive $CD4^+$ T cells have been shown to be potent producers of γ-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan & Kaufmann, *Tuberculosis: Pathogenesis, Protection and Control* (Bloom ed., 1994), *Tuberculosis* (2nd ed., Rom and Garay, eds., 2003), and *Harrison's Principles of Internal Medicine*, Chapter 150, pp. 953-966 (16th ed., Braunwald, et al., eds., 2005).

There remains a need for effective treatment strategies to prevent reactivation of *Mycobacterium tuberculosis* infections, from both active and latent infections. This invention fulfills this and other needs.

DESCRIPTION OF THE LISTED SEQUENCES

SEQ ID No:1: Mtb72f with N-terminal 6 His tag (DNA)

SEQ ID No:2: Mtb72f with N-terminal 6 His tag (protein)

SEQ ID No:3: M72 (variant of Mtb72f) with N-terminal 2 His insertion (DNA)

SEQ ID No:4: M72 (variant of Mtb72f) with N-terminal 2-His insertion (protein)

SEQ ID No:5: Mtb72f without N-terminal His insertion (DNA)

SEQ ID No:6: Mtb72f without N-terminal His insertion (protein)

BRIEF SUMMARY OF THE INVENTION

The present invention provides pharmaceutical compositions comprising a Mtb72f fusion protein or an immunogenic fragment thereof from a *Mycobacterium* species of the tuberculosis complex, for example together with one or more adjuvants, including AS01B and AS02A.

The present invention is based, in part, on the inventors' discovery that administration of a Mtb72f fusion protein or immunogenic fragment thereof eg together with one or more adjuvants or a nucleic acid encoding a Mtb72f fusion protein or immunogenic fragment thereof can prevent or treat reactivation of an active or inactive *M. tuberculosis* infection. In a preferred embodiment, a Mtb72f fusion protein or nucleic acid is administrated with one or more chemotherapeutic agents effective against a *M. tuberculosis* infection.

In one aspect, the compositions are employed in methods for preventing or treating tuberculosis reactivation in a subject, the method comprising the step of administering to a mammal already infected with *Mycobacterium tuberculo-* sis an immunologically effective amount of a pharmaceutical composition comprising a Mtb72f fusion protein or an immunogenic fragment thereof from a *Mycobacterium* species of the tuberculosis complex and an adjuvant, wherein the Mtb72f fusion protein induces an immune response against *M. tuberculosis*, thereby preventing or treating tuberculosis reactivation.

In another aspect, the compositions are employed in methods for preventing tuberculosis reactivation in a subject, the method comprising the step of administering to a mammal already infected with *Mycobacterium tuberculosis* an immunologically effective amount of a pharmaceutical composition comprising a nucleic acid encoding a Mtb72f fusion protein or an immunogenic fragment thereof from a *Mycobacterium* species of the tuberculosis complex, wherein the expressed Mtb72f fusion protein induces an immune response against *M. tuberculosis*, thereby preventing or treating tuberculosis reactivation.

In another aspect, the compositions are employed in methods for reducing the time course of chemotherapy against a *M. tuberculosis* infection, the method comprising administering to a mammal already infected with *Mycobacterium tuberculosis* one or more chemotherapeutic agents effective against a *M. tuberculosis* infection and an immunologically effective amount of a pharmaceutical composition comprising a Mtb72f fusion protein or an immunogenic fragment thereof from a *Mycobacterium* species of the tuberculosis complex and an adjuvant, wherein said Mtb72f fusion protein or immunogenic fragment thereof induces an immune response against *M. tuberculosis*, thereby allowing for reducing the time course of chemotherapy against a *M. tuberculosis* infection. By shortening the time course of chemotherapy against a *M. tuberculosis* infection, the present methods are also effective in enhancing the compliance of an individual being treated for a *M. tuberculosis* infection in completing an entire course of treatment.

BRIEF DESCRIPTION OF THE DRAWINGS

(FIG. 2A, FIG. 2B, FIG. 2C) Ten days after the last immunization the mice were bled and sera tested for anti-Mtb72f antibody response for both IgG1 and IgG2a isotopes by ELISA.

(FIG. 3A, FIG. 3B) Ten days after the last immunization the mice were bled and sera tested for anti-Mtb72f antibody response for both IgG1 and IgG2a isotopes by ELISA.

(FIG. 4D, FIG. 4F) As controls, splenocyte cultures were also stimulated with either PPD (3 g/ml)(FIG. 4E), BCG Lysate (10 g/ml)(FIG. 4G), conA (3 g/ml) (FIG. 4C) or medium alone (FIG. 4A). IFN-γ production was subsequently measured by ELISA.

FIG. 6A.1-FIG. 6A.4; FIG. 6B1-FIG. 6B.4 shows CD4+ T cell and IFN-γ cytokine responses in *M. tuberculosis* infected SWR/J mice treated with chemotherapy and then immunized with Mtb72f (72f). Spleen cells were obtained from mice at varying timepoints and stimulated in vitro overnight with 10 g/ml of rMtb72f. The cells were then stained for CD4 and IFN-γ. As a control, splenocyte cultures were also stimulated with medium alone. CD4+ T cell specific IFN-γ+ production was subsequently measured by intracellular cytokine staining (ICS).

DETAILED DESCRIPTION OF SPECIFIC EMBODIMENTS

Figure 1:
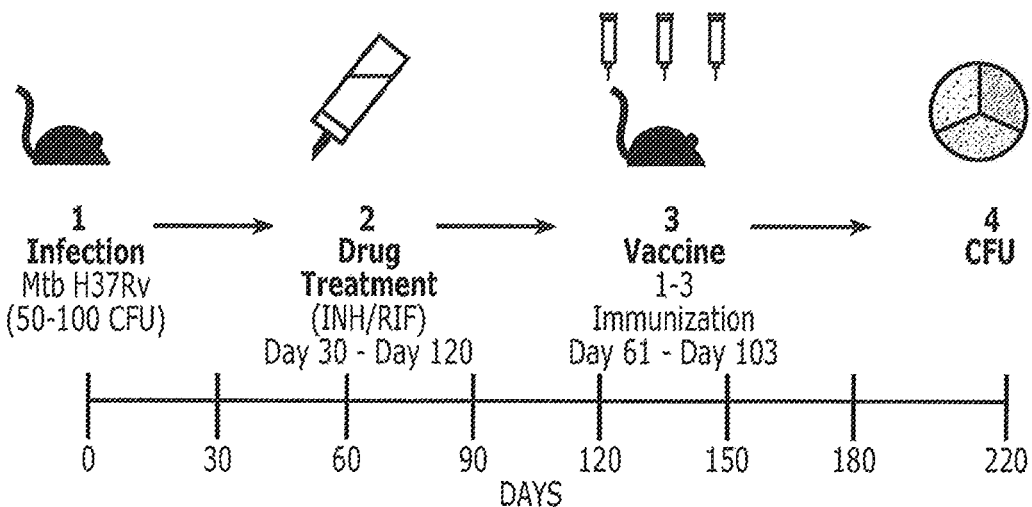
FIG. 1 shows a graphic representation of the *M. tuberculosis* reactivation model in Swiss Webster mice (SWR/J). The figure shows timepoints for infection, chemotherapy treatment (50 mg rifampin/85 mg isoniazide per Liter of drinking water), immunizations and enumeration of bacterial load/colony forming units (CFU).
Figure 2A:
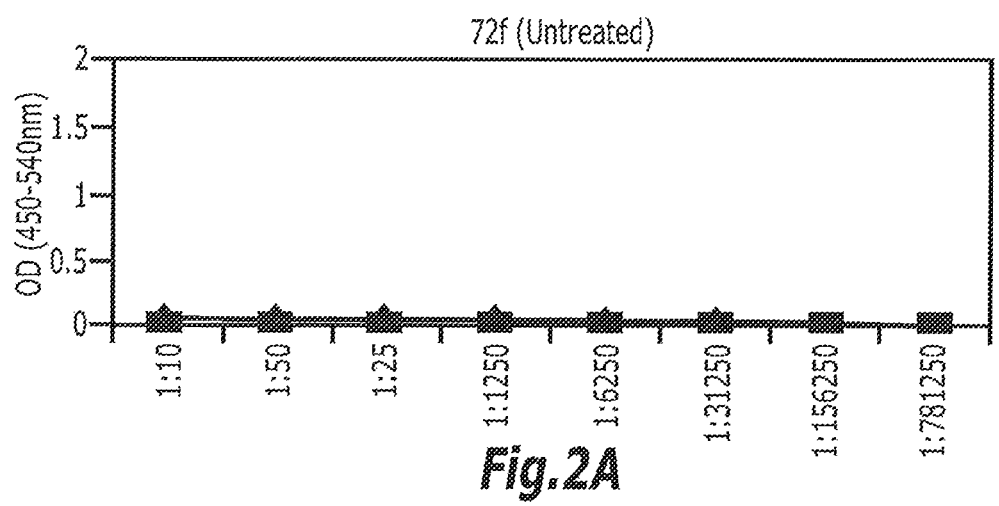
FIG. 2A-2C show IgG1 and IgG2a antibody responses in *M. tuberculosis* infected SWR/J mic treated with chemotherapy and then immunized with Mtb72f (72f). Mice were left untreated, treated with chemotherapy (50 mg rifampin/85 mg isoniazide per Liter of drinking water) or treated with chemotherapy and immunized three times intra-muscularly with 8 µg per dose of Mtb72f formulated without adjuvant.
Figure 2B:
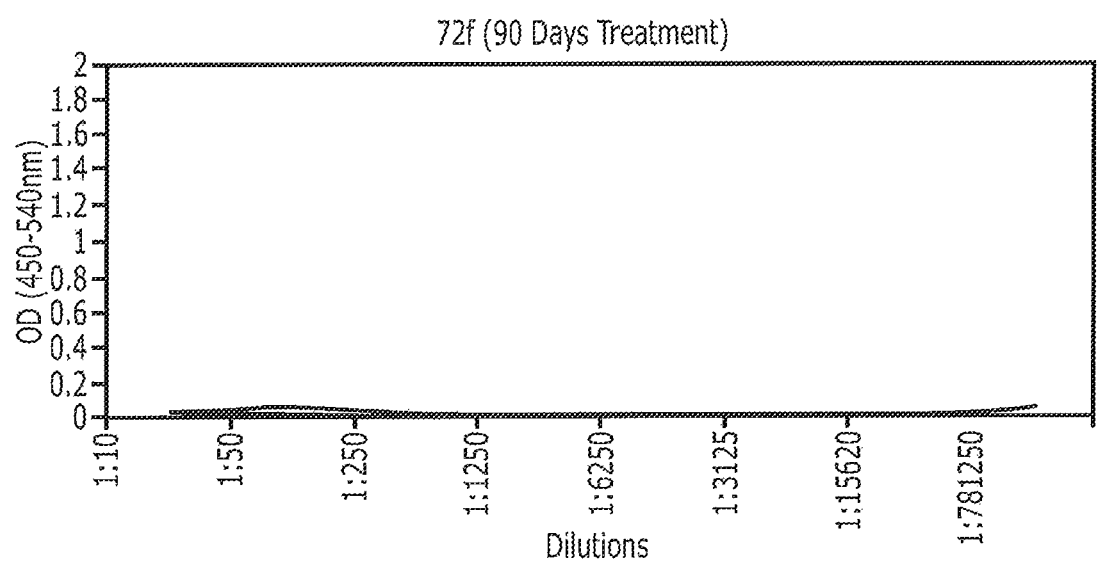
Figure 2C:
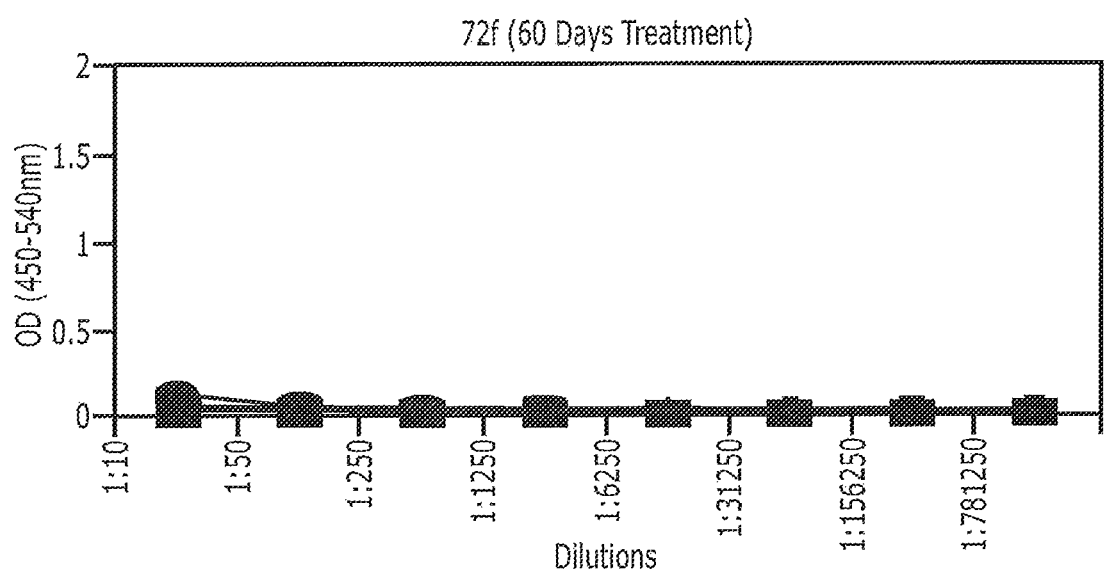
Figure 3A:
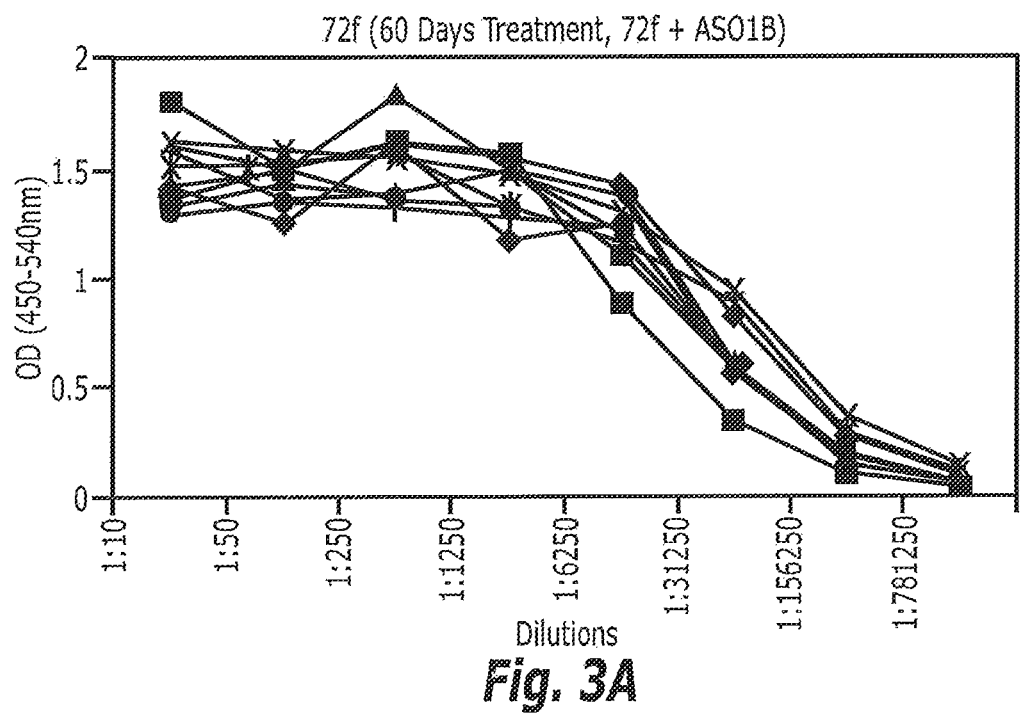
FIG. 3A-3B show IgG1 and IgG2a antibody responses in *M. tuberculosis* infected SWR/J mice treated with chemotherapy and then immunized with Mtb72f (72f). Mice were left untreated, treated with chemotherapy (50 mg rifampin/85 mg isoniazide per Liter of drinking water) or treated with chemotherapy and immunized three times intra-muscularly with 8 µg per dose of Mtb72f formulated with the adjuvant AS01B.
Figure 3B:
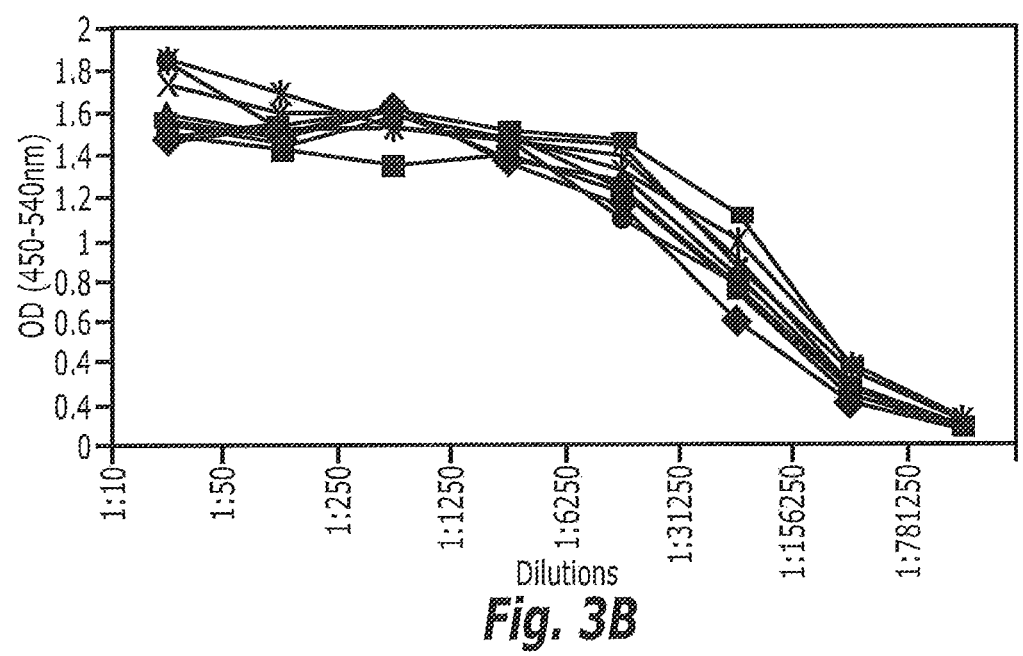
Figure 4A:
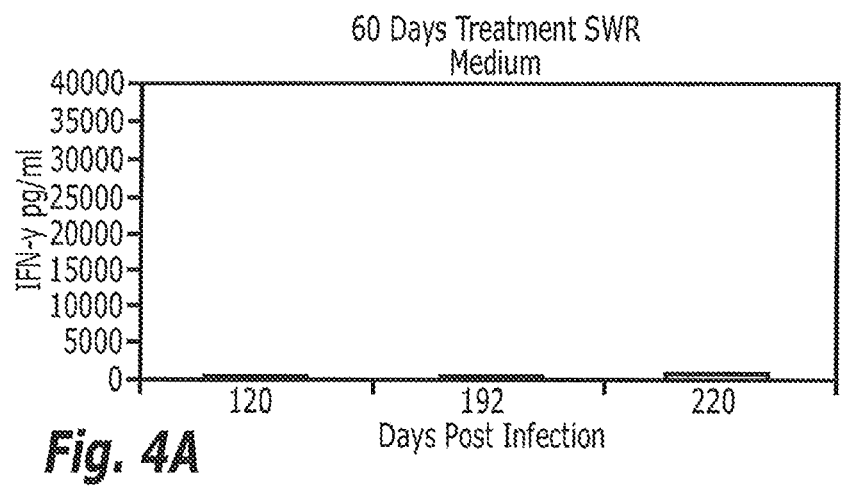
FIG. 4A-4G show interferon-gamma (IFN-γ) responses in *M. tuberculosis* infected SWR/J mice treated with chemotherapy and then immunized with Mtb72f (72f). Spleen cells were obtained from mice at varying timepoints and stimulated in vitro for three days with 10 µg/ml of either rMtb72f (FIG. 4B) or the components (Mtb32c (MtbRa12) and Mtb39 (MtbTbH9)) as indicated.
Figure 4B:
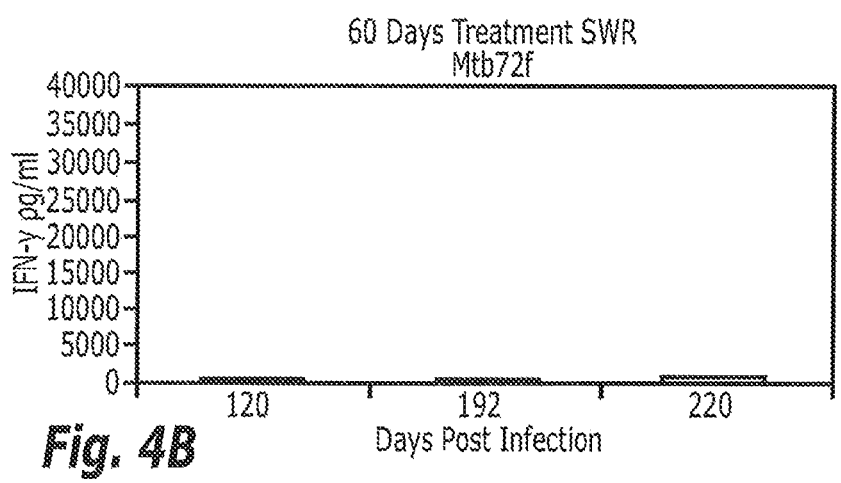
Figure 4C:
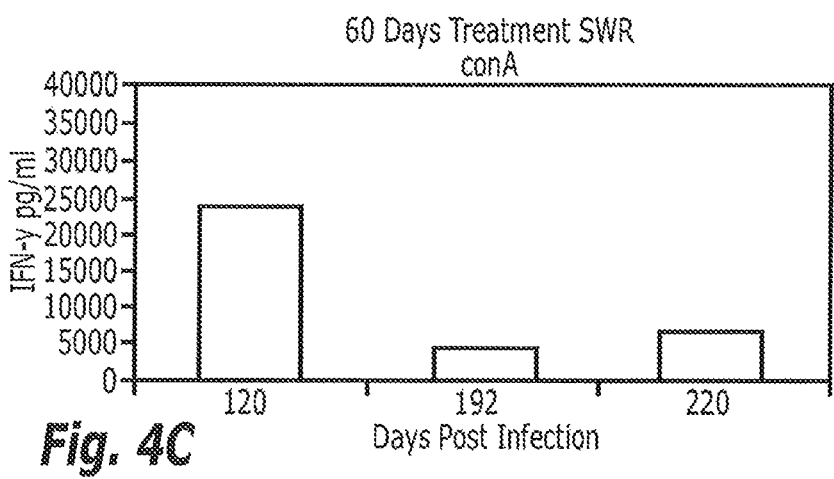
Figure 4D:
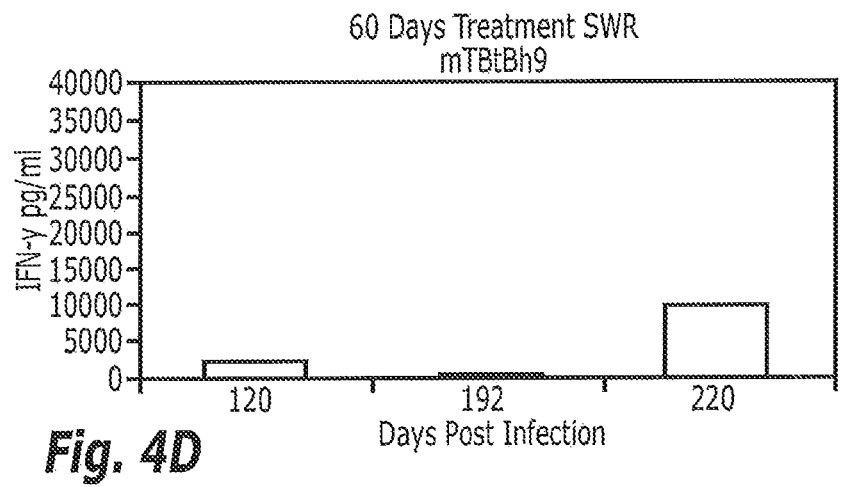
Figure 4E:
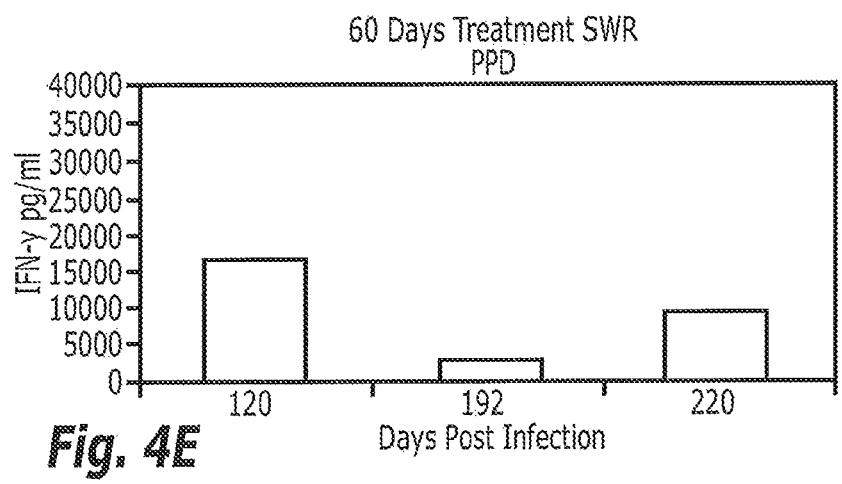
Figure 4F:
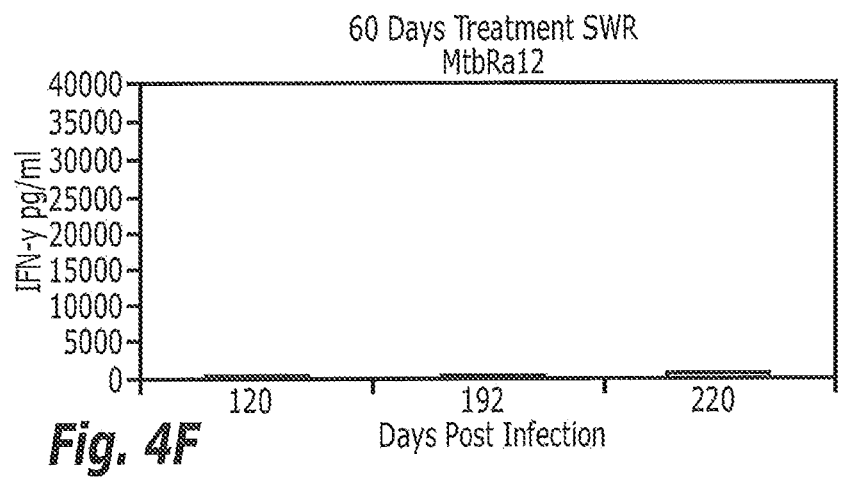
Figure 4G:
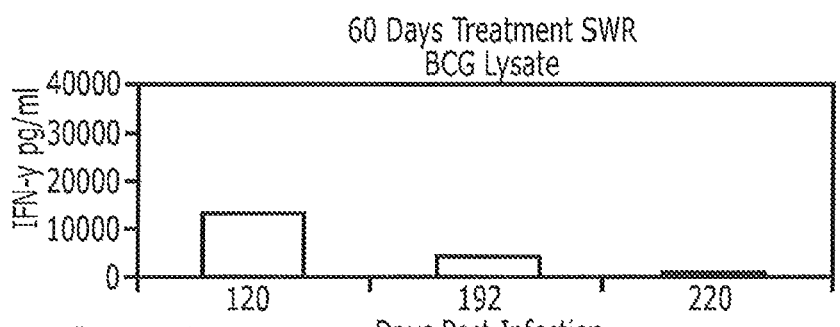
Figure 5A:
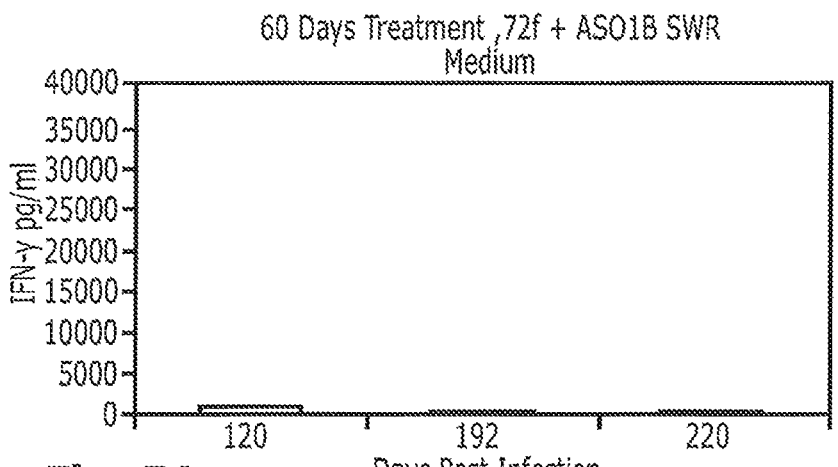
FIG. 5A-5G show IFN-γ responses in *M. tuberculosis* infected SWR/J mice treated with chemotherapy and then immunized with Mtb72f (72f). Spleen cells were obtained from mice at varying timepoints and stimulated in vitro for three days with 10 g/ml of either rMtb72f (FIG. 5B) or the components (Mtb32c (MtbRa12) and Mtb39 (MtbTbH9)) as indicated (FIG. 5D, FIG. 5F). As controls, splenocyte cultures were also stimulated with either PPD (3 g/ml)(FIG. 5E), BCG Lysate (10 g/ml)(FIG. 5G), conA (3 g/ml)(FIG. 5C) or medium alone (FIG. 5A). IFN-γ production was subsequently measured by ELISA.
Figure 5B:
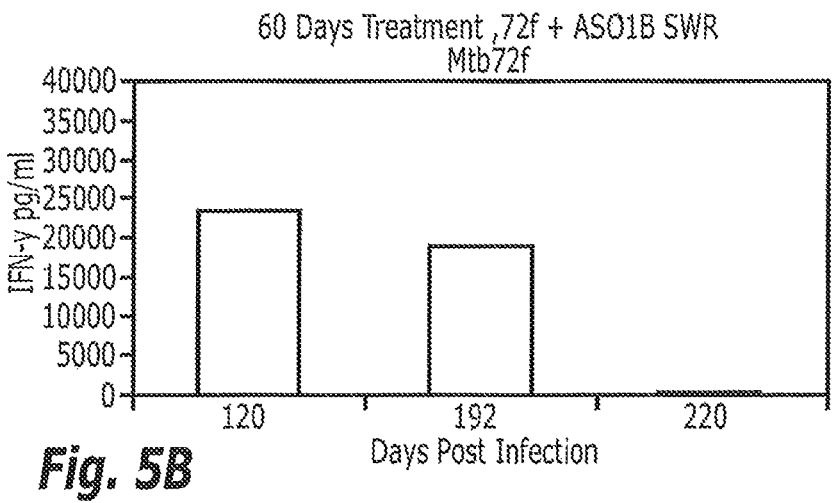
Figure 5C:
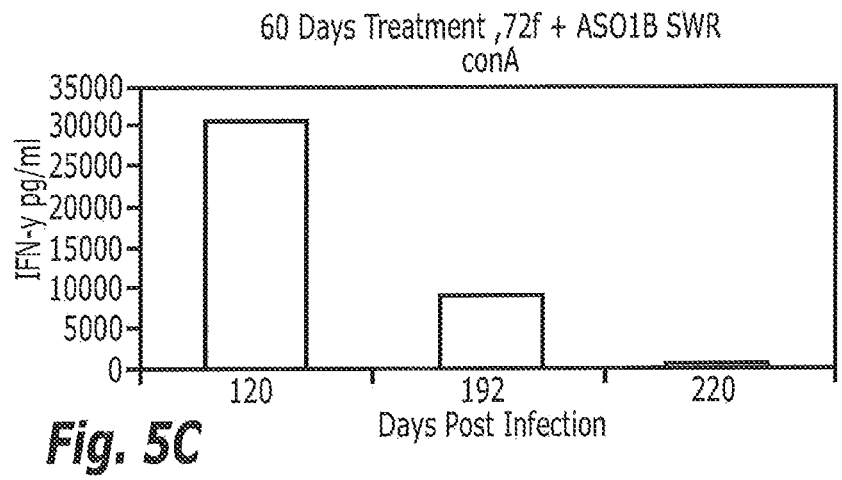
Figure 5D:
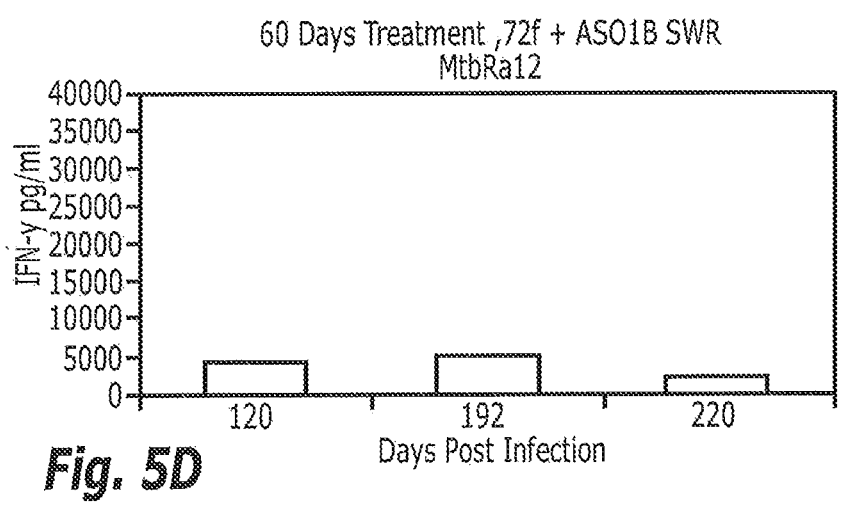
Figure 5E:
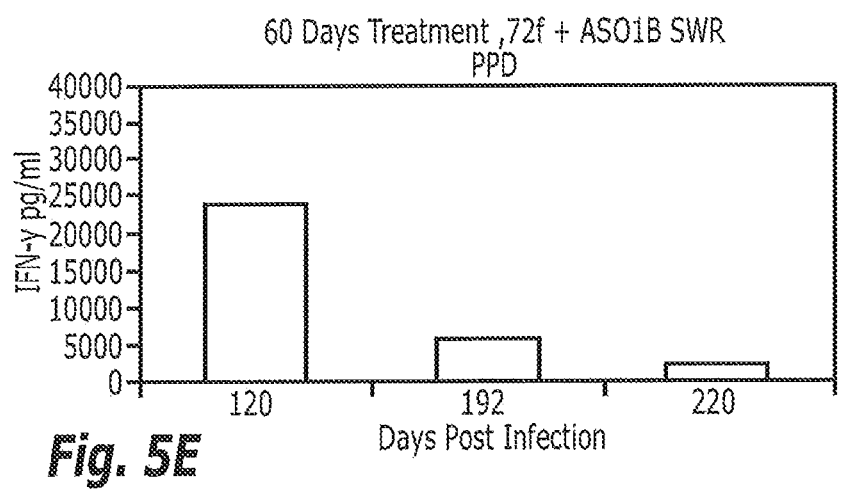
Figure 5F:
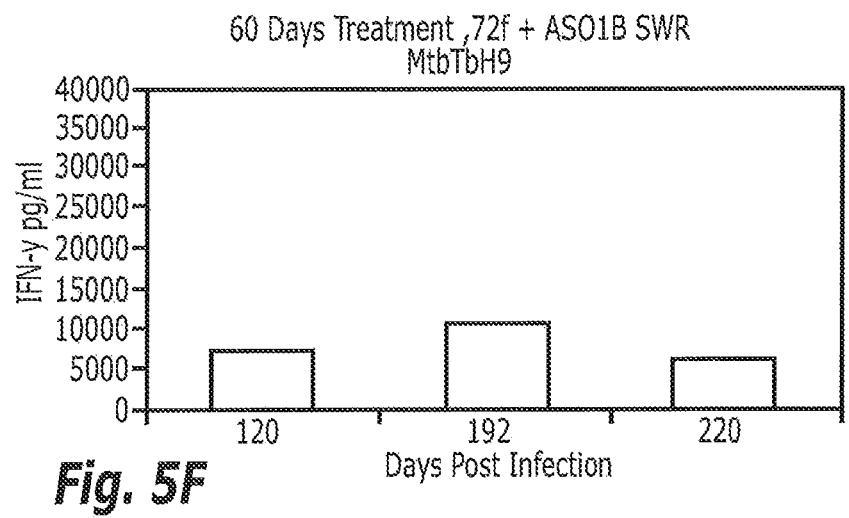
Figure 5G:
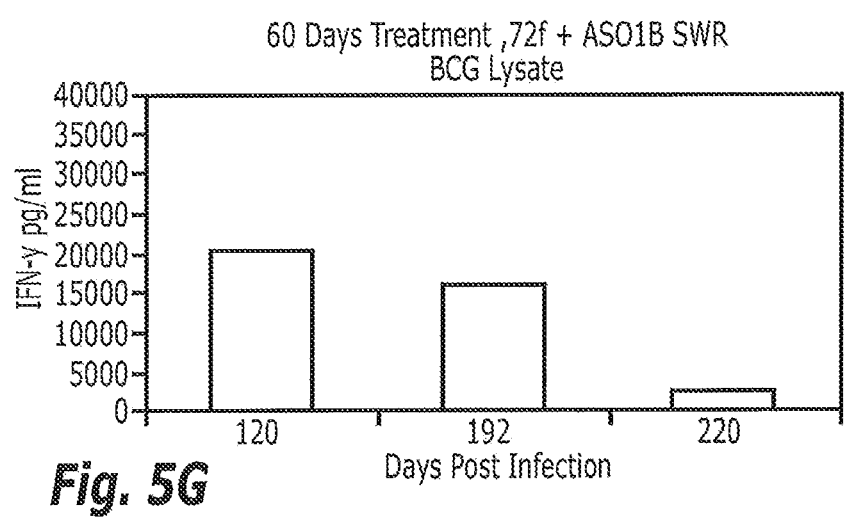
Figures 7, 8:
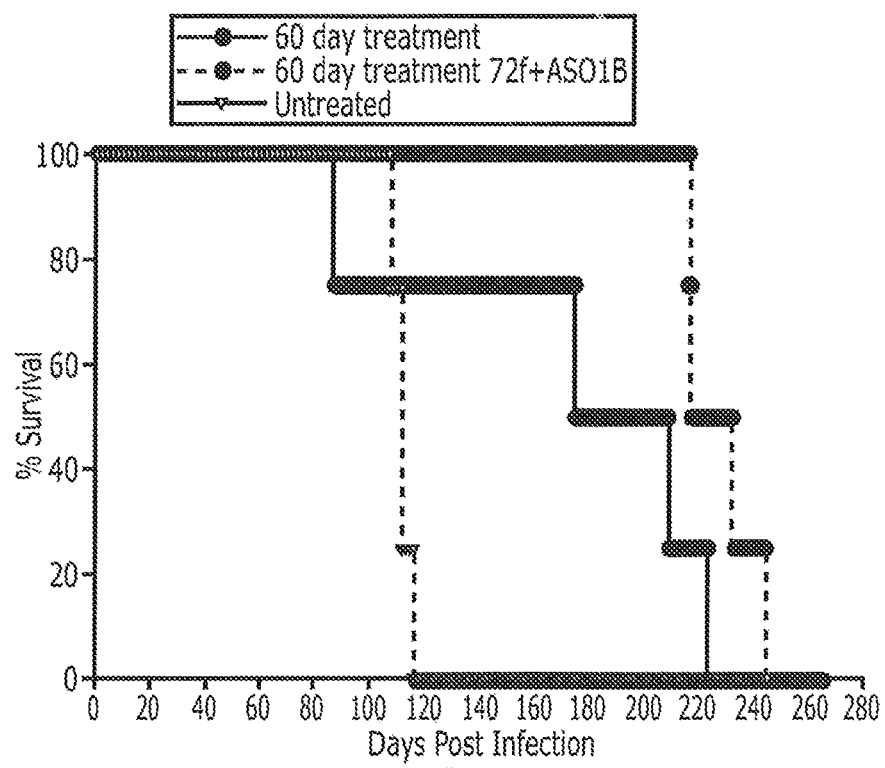
FIG. 7 shows a tabular summary of the values of CD4+ and CD8+ T cell specific IFN-γ+ production at Day 120 after Mtb infection. Spleen cells were obtained from groups of mice left untreated, treated with 30, 60 or 90 days of combination chemotherapy, or treated with combination chemotherapy as an adjunct to the Mtb72f (72f) vaccine. Splenocytes were stimulated in vitro overnight with 10 g/ml of rMtb72f. The cells were then stained for CD4, CD8 or IFN-γ. As a control, splenocyte cultures were also stimulated with medium alone. CD4+ and CD8+ T cell specific IFN-γ+ production was subsequently measured by intracellular cytokine staining.
FIG. 8 shows survival of *M. tuberculosis* infected SWR/J mice treated with chemotherapy and then immunized with Mtb72f (72f). Mice were infected via aerosol with 50-100 CFU of MtbH37Rv and chemotherapy (50 mg rifampin/85 mg isoniazide per Liter of drinking water) was started in a subset of mice thirty days later. Chemotherapy was continued for 60 days. Half of those mice receiving chemotherapy were immunized three times intra-muscularly with 8 µg per dose of Mtb72f formulated with the adjuvant AS01B.
Figure 9:
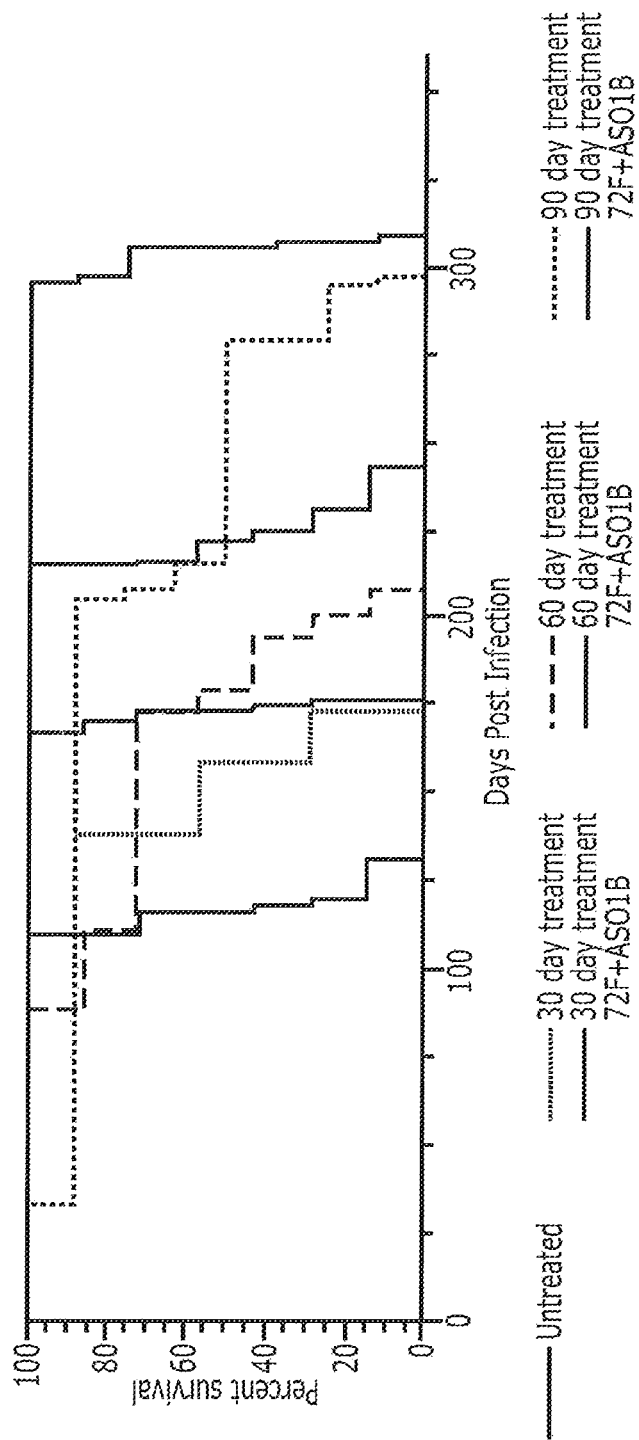
FIG. 9 shows survival of *M. tuberculosis* infected SWR/J mice treated with chemotherapy and then immunized with Mtb72f (72f). Mice were infected via aerosol with 50-100 CFU of MtbH37Rv and chemotherapy (50 mg rifampin/85 mg isoniazide per Liter of drinking water) was started in a subset of mice thirty days later. Chemotherapy was continued for 30, 60 or 90 days in separate subsets of mice. Half of those mice receiving chemotherapy were immunized three times intra-muscularly with 8 µg per dose of Mtb72f formulated with the adjuvant AS01B.

The present invention relates to compositions comprising Mtb72f nucleic acids or fusion proteins and an adjuvant useful for treating, preventing, or delaying reactivation of an active or inactive (i.e., latent) *Mycobacterium* infection, and methods for their use. More specifically, the compositions of the present invention comprise Mtb72f fusion polypeptides or immunogenic fragments thereof or nucleic acids encoding Mtb72f fusion polypeptides or immunogenic fragments thereof having components from a *Mycobacterium* species of the tuberculosis complex, e.g., a species such as *M. tuberculosis, M. bovis*, or *M. africanum*, or a *Mycobacterium* species that is environmental or opportunistic and that causes opportunistic infections such as lung infections in immune compromised hosts (e.g., patients with AIDS), e.g., BCG, *M. avium, M. intracellulare, M. celatum, M. genavense, M. haemophilum, M. kansasii, M. simiae, M. vaccae, M. fortuitum*, and *M. scrofulaceum* (see, e.g., *Harrison's Principles of Internal Medicine*, Chapter 150, pp. 953-966 (16th ed., Braunwald, et al., eds., 2005). The inventors of the present application surprisingly discovered that compositions comprising Mtb72f fusion polypeptides or nucleic acids encoding Mtb72f fusion polypeptides, or immunogenic fragments thereof, are useful in treating, preventing or delaying reactivation of a *M. tuberculosis* infection. In a preferred embodiment, a Mtb72f fusion polypeptide or nucleic acid is administered with one or more chemotherapeutic agents.

These compositions, polypeptides, and the nucleic acids that encode them are therefore useful for eliciting an immune response in mammals that is protective against reactivation of disease symptoms.

The Mtb72f nucleic acids and fusion polypeptides of the present invention can further comprise other components designed to enhance their antigenicity or to improve these antigens in other aspects. For example, improved isolation of the fusion polypeptide antigens may be facilitated through the addition of a stretch of histidine residues towards one end of the antigen. The compositions, polypeptides, and nucleic acids of the invention can comprise additional copies of antigens, or additional heterologous polypeptides from *Mycobacterium* sp., such as MTB8.4 antigen, MTB9.8 antigen, MTB9.9 antigen, MTB40 antigen, MTB41 antigen, ESAT-6 antigen, MTB85 complex antigen, α-crystalline antigen, or NS1 antigen. Alternatively or in addition, the compositions, polypeptides, and nucleic acids of the invention can comprise additional copies of other antigens from *Mycobacterium* sp., such as Ag85B or MTCC #2. The compositions, polypeptides, and nucleic acids of the invention can also comprise additional polypeptides from other sources. For example, the compositions and fusion proteins of the invention can include polypeptides or nucleic acids encoding polypeptides, wherein the polypeptide enhances expression of the antigen, e.g., NS1, an influenza virus protein (see, e.g. WO99/40188 and WO93/04175). The nucleic acids of the invention can be engineered based on codon preference in a species of choice, e.g., humans.

The Mtb72f fusion protein compositions usually comprise one or more adjuvants, e.g., AS01B (monophosphoryl lipid A (MPL) and QS21 in a liposome formulation; see, U.S. Patent Publication No. 2003/0143240); AS02A (3D-MPL and QS21 and an oil in water emulsion; see, Bojang, et al., *Lancet* (2001) 358:1927); ENHANZYN (Detox); 3D-MPL; saponins including Quil A and its components eg QS21 and saponin mimetics; CWS; TDM; AGP; immunostimulatory oligonucleotides eg CPG; Leif and derivatives thereof. In a preferred embodiment, a Mtb72f fusion polypeptide is administered with one or more adjuvants selected from the group consisting of 3D-MPL and QS21 in a liposome formulation e.g. AS01B and MPL and QS21 and an oil in water emulsion (e.g. AS02A). Adjuvants AS01B and AS02A are further described in Pichyangkul, et al., *Vaccine* (2004) 22:3831-40.

When delivering the Mtb72f antigen as a nucleic acid, it can be delivered, for example, in a viral vector (i.e., an adenovirus vector), or in a mutant bacterium host cell (i.e., a mutant, avirulent *Mycobacterium, Lactobacillus* or *Bacillus* host cell including *Bacillus* Calmette-Guerin (BCG) and *Lactococcus lactis*).

In one aspect, the compositions are employed in methods for preventing or treating tuberculosis reactivation in a subject, the method comprising the step of administering to a mammal already infected with *Mycobacterium tuberculosis* an immunologically effective amount of a pharmaceutical composition comprising a Mtb72f fusion protein or an immunogenic fragment thereof from a *Mycobacterium* species of the tuberculosis complex and an adjuvant, wherein the Mtb72f fusion protein induces an immune response against *M. tuberculosis*, thereby preventing tuberculosis reactivation. By practicing the methods of the present invention, reactivation of a *M. tuberculosis* infection can be delayed (for example by a period of months, years or indefinitely).

In one aspect, the compositions are employed in methods for preventing or treating tuberculosis reactivation in a subject, the method comprising the step of administering to a mammal already infected with *Mycobacterium tuberculosis* an immunologically effective amount of a pharmaceutical composition comprising a nucleic acid encoding a Mtb72f fusion protein or an immunogenic fragment thereof from a *Mycobacterium* species of the tuberculosis complex, wherein the expressed Mtb72f fusion protein induces an immune response against *M. tuberculosis*, thereby preventing tuberculosis reactivation.

In one embodiment, the Mtb72f nucleic acid or fusion protein is administered to an individual with an active *M. tuberculosis* infection. In one embodiment, the Mtb72f nucleic acid or fusion protein is administered to an individual with an inactive or latent *M. tuberculosis* infection. In one embodiment, the Mtb72f nucleic acid or fusion protein is administered to an individual infected with a multi-drug resistant strain of *M. tuberculosis*. In one embodiment, the Mtb72f nucleic acid or fusion protein is administered to an individual who was previously immunized with *Bacillus* Calmette-Guerin (BCG).

In some embodiments, the Mtb72f nucleic acid or fusion protein is administered with one or more chemotherapeutic agents effective against a *M. tuberculosis* infection. Examples of such chemotherapeutic agents include, but are not limited to, amikacin, aminosalicylic acid, capreomycin, cycloserine, ethambutol, ethionamide, isoniazid, kanamycin, pyrazinamide, rifamycins (i.e., rifampin, rifapentine and rifabutin), streptomycin, ofloxacin, ciprofloxacin, clarithromycin, azithromycin and fluoroquinolones. Such chemotherapy is determined by the judgment of the treating physician using preferred drug combinations. "First-line" chemotherapeutic agents used to treat a *M. tuberculosis* infection that is not drug resistant include isoniazid, rifampin, ethambutol, streptomycin and pyrazinamide. "Second-line" chemotherapeutic agents used to treat a *M. tuberculosis* infection that has demonstrated drug resistance to one or more "first-line" drugs include ofloxacin, ciprofloxacin, ethionamide, aminosalicylic acid, cycloserine, amikacin, kanamycin and capreomycin.

The Mtb72f nucleic acid or fusion protein can be administered before, concurrently with, or after administration of the one or more chemotherapeutic agents effective against a

*M. tuberculosis* infection. In one embodiment, the Mtb72f nucleic acid or fusion protein is administered about 2 weeks after commencing administration of one or more chemotherapeutic agents. The one or more chemotherapeutic agents are generally administered over a period of time, for example, for about 1, 2, 3, or 4 weeks, 2, 3, 4, 5, 6 or 8 months, 1 year or longer.

In certain embodiments, the effect of an Mtb72f nucleic acid or fusion protein is enhanced by administration with *Bacillus* Calmette-Guerin (BCG).

In some embodiments, a priming or first administration of a Mtb72f nucleic acid or fusion polypeptide is followed by one or more "boosting" or subsequent administrations of a Mtb72f nucleic acid or fusion polypeptide ("prime and boost" method). For instance, a first administration with a Mtb72f nucleic acid or fusion polypeptide is followed by one or more subsequent administrations of a Mtb72f nucleic acid or fusion protein. In one embodiment, a first administration with a Mtb72f nucleic acid or fusion polypeptide is followed by one or more subsequent administrations of a Mtb72f fusion polypeptide. In one embodiment, a first administration with a Mtb72f nucleic acid or fusion polypeptide is followed by one or more subsequent administrations of a Mtb72f nucleic acid. Usually the first or "priming" administration and the second or "boosting" administration are given about 2-12 weeks apart, or up to 4-6 months apart. Subsequent "booster" administrations are given about 6 months apart, or as long as 1, 2, 3, 4 or 5 years apart. Conventional booster treatment (e.g., a protein priming administration followed by a protein boosting administration) is also useful in preventing or treating against *M. tuberculosis* reactivation.

In another aspect, the compositions are employed in methods for reducing or shortening the time course of chemotherapy against a *M. tuberculosis* infection, the method comprising administering to a mammal already infected with *Mycobacterium tuberculosis* one or more chemotherapeutic agents effective against a *M. tuberculosis* infection and an immunologically effective amount of a pharmaceutical composition comprising a Mtb72f fusion polypeptide or an immunogenic fragment thereof from a *Mycobacterium* species of the tuberculosis complex and an adjuvant, wherein said Mtb72f fusion polypeptide induces an immune response against *M. tuberculosis*, thereby allowing for reducing or shortening the time course of chemotherapy against a *M. tuberculosis* infection. Usually, administration of a Mtb72f nucleic acid or fusion polypeptide will allow effective chemotherapeutic treatment against a *M. tuberculosis* infection within 6 months, 5 months, 4 months, 3 months, or less.

The Mtb72f compositions are usually administered to humans, but are effective in other mammals including domestic mammals (i.e., dogs, cats, rabbits, rats, mice, guinea pigs, hamsters, chinchillas) and agricultural mammals (i.e., cows, pigs, sheep, goats, horses).

In its most general respect, a Mtb72f fusion protein according to the invention is a protein comprising at least an immunogenic fragment of each of the 3 antigens Ra12-TbH9-Ra35.

In the nomenclature of the application, Ra35 refers to the N-terminus of Mtb32A (Ra35FL), comprising at least about the first 205 amino acids of Mtb32A from *M. tuberculosis*, the nucleotide and amino acid sequence of which is disclosed in FIG. 4 of U.S. Pat. No. 7,186,412, or the corresponding region from another *Mycobacterium* species. Most typically, Ra35 refers to the portion of SEQ ID No: 2 disclosed in the present application corresponding to residues 535-729. Alternatively it refers to a variant on Ra35 in which the amino acid Ser corresponding to 710 in SEQ ID No: 2 is replaced with Ala.

Ra12 refers to the C-terminus of Mtb32A (Ra35FL), comprising at least about the last 132 amino acids from MTB32A from *M. tuberculosis*, the sequence of which is disclosed as SEQ ID NO:4 (DNA) and SEQ ID NO:66 (predicted amino acid sequence) in the U.S. Pat. No. 6,592,877, or the corresponding region from another *Mycobacterium* species. Most typically, Ra12 refers to the portion of SEQ ID No: 2 disclosed in the present application corresponding to residues 8-139.

Mtb39 (TbH9) refers to a sequence essentially that which is disclosed as SEQ ID NO: 106 (cDNA full length) and SEQ ID NO: 107 (protein full length) in the U.S. patent application Ser. No. 08/658,800, Ser. No. 08/659,683, U.S. Pat. Nos. 6,290,969, and 6,338,852 and in the WO97/09428 and WO97/09429 applications. The sequence is also disclosed as SEQ ID NO:33 (DNA) and SEQ ID NO:91 (amino acid) in U.S. Pat. No. 5,946,926. Most typically, TbH9 refers to the portion of SEQ ID No: 2 disclosed in the present application corresponding to residues 143-532.

The following provides sequences of some individual antigens used in the compositions and fusion proteins of the invention:

Mtb32A (TbRa35FL or Ra35FL), the sequence of which is disclosed as SEQ ID NO:17 (cDNA) and SEQ ID NO:79 (protein) in the U.S. patent application Ser. Nos. 08/523,436, 08/523,435, Ser. No. 08/658,800, Ser. No. 08/659,683, U.S. Pat. Nos. 6,290,969, 6,350,456, and 6,338,852 and in the WO97/09428 and WO97/09429 applications, see also Skeiky et al., *Infection and Immunity* 67:3998-4007 (1999);

The following provides sequences of some fusion proteins of the invention:

TbH9-Ra35 (Mtb59F), the sequence of which is disclosed as SEQ ID NO:23 (cDNA) and SEQ ID NO:24 (protein) in the U.S. Pat. No. 6,627,198 and in WO199951748;

Ra12-TbH9-Ra35 (Mtb72f), the sequence of which is disclosed as SEQ ID NO:1 or SEQ ID NO: 5 (DNA) and SEQ ID NO:2 or SEQ ID NO:6 (protein) in the present application, as well as in U.S. Pat. No. 6,544,522, and in WO199951748. The sequences of SEQ ID NO: 1 and SEQ ID NO:2 include a His tag of 6 His residues.

M72 which is a mutant of Mtb72f in which the serine residue at amino acid corresponding to position 710 in SEQ ID No: 2 has been changed to Ala, (as well as 4 His residues having been removed from the His-tag at the N terminus) the sequence of which is disclosed as SEQ ID No: 3 (DNA) and SEQ ID No: 4 (protein) in the present application. A variant on these sequences in which the protein has a His tag of 6 His residues is disclosed in U.S. Pat. No. 7,186,412 and in WO2001098460. By virtue of the replacement of Ser710 with Ala, M72 is believed to be more resistant to autolysis than Mtb72f.

The following provides sequences of some additional antigens used in the compositions and fusion proteins of the invention:

Mtb8.4 (DPV), the sequence of which is disclosed as SEQ ID NO:101 (cDNA) and SEQ ID NO:102 (protein) in the U.S. patent application Ser. No. 08/658,800, Ser. No. 08/659,683, U.S.

U.S. Pat. Nos. 6,290,969 and 6,338,852 and in the WO97/09428 and WO97/09429 applications;

Mtb9.8 (MSL), the sequence of which is disclosed as SEQ ID NO: 12 (DNA), SEQ ID NO:109 (predicted amino acid sequence) and SEQ ID NO:110 to 124 (peptides) in the U.S. patent application Ser. No. 08/859,381, Ser. No. 08/858,998, U.S. Pat. Nos. 6,555,653 and 6,613,881 and in WO199853075 and WO98053076;

Mtb9.9A (MTI, also known as MTI-A), the sequence of which is disclosed as SEQ ID NO:3 and SEQ ID NO:4 (DNA) and SEQ ID NO:29 and SEQ ID NO:51 to 66 (ORF peptide for MTI) in the U.S. patent application Ser. No. 08/859,381, Ser. No. 08/858,998, U.S. Pat. Nos. 6,555,653 and 6,613,881 and in WO199853075 and WO98053076. Two other MTI variants also exist, called MTI-B and MTI-C;

Mtb40 (HTCC #1), the sequence of which is disclosed as SEQ ID NO:137 (cDNA) and 138 (predicted amino acid sequence) in the U.S. Pat. Nos. 6,555,653 and 6,613,881 and in WO199853075 and WO98053076;

Mtb41 (MTCC #2), the sequence of which is disclosed as SEQ ID NO: 140 (cDNA) and SEQ ID NO: 142 (predicted amino acid sequence) in the U.S. Pat. Nos. 6,555,653 and 6,613,881 and WO199853075 and WO98053076;

ESAT-6, the sequence of which is disclosed as SEQ ID NO:103 (DNA) and SEQ ID NO:104 (predicted amino acid sequence) in the U.S. Pat. No. 6,592,877. The sequence of ESAT-6 is also disclosed in U.S. Pat. No. 5,955,077;

α-crystalline antigen, the sequence of which is disclosed in Verbon et al., *J. Bact.* 174:1352-1359 (1992);

85 complex antigen, the sequence of which is disclosed in Content et al., *Infect. & Immunol.* 59:3205-3212 (1991).

Each of the above sequences is also disclosed in Cole et al. *Nature* 393:537 (1998) and can be found at, e.g., www.sanger.ac.uk and www.pasteur.fr/mycdb/.

The above sequences are disclosed in U.S. patent application Ser. Nos. 08/523,435, 08/523,436, 08/658,800, 08/659,683, 08/942,341, 08/942,578, 08/858,998, and 08/859,381, U.S. Pat. Nos. 6,338,852, 6,290,969, 6,350,456, 6,458,366, 6,592,877, 6,555,653, 6,613,881, 6,544,522, and 6,627,198 and in WO 1998/53075, WO 1998/53076, WO 1999/42118, WO 1999/42076, WO 1999/51748, WO97/09428 and WO97/09429, WO98/16645, WO98/16646, each of which is herein incorporated by reference.

The antigens described herein include polymorphic variants and conservatively modified variations, as well as inter-strain and interspecies *Mycobacterium* homologs. In addition, the antigens described herein include subsequences or truncated sequences. The fusion proteins may also contain additional polypeptides, optionally heterologous peptides from *Mycobacterium* or other sources. These antigens may be modified, for example, by adding linker peptide sequences as described below. These linker peptides may be inserted between one or more components which make up each of the fusion proteins.

Definitions

The term "tuberculosis reactivation" refers to the later manifestation of disease symptoms in an individual that tests positive in a tuberculin test but does not have apparent disease symptoms. The individual is infected with *M. tuberculosis*, and may or may not have previously manifested active disease symptoms that had been treated sufficiently to bring the tuberculosis into an inactive or latent state. Methods for the prevention or treatment of tuberculosis reactivation can be initiated in an individual manifesting active symptoms of disease, however.

"Primary tuberculosis" refers to clinical illness (manifestation of disease symptoms) directly following infection with *M. tuberculosis*. See, *Harrison's Principles of Internal Medicine*, Chapter 150, pp. 953-966 (16th ed., Braunwald, et al., eds., 2005).

"Secondary tuberculosis" or "postprimary tuberculosis" refers to the reactivation of a dormant, inactive or latent *M. tuberculosis* infection. See, Harrison's Principles of Internal Medicine, supra.

An "active infection of *M. tuberculosis*" refers to a *M. tuberculosis* infection with manifested disease symptoms.

An "inactive, dormant or latent infection of *M. tuberculosis*" refers to a *M. tuberculosis* infection without manifested disease symptoms.

A "drug resistant" *M. tuberculosis* infection refers to a *M. tuberculosis* infection wherein the infecting strain is not held static or killed (is resistant to) one or more of so-called "front-line" chemotherapeutic agents effective in treating a *M. tuberculosis* infection (e.g., isoniazid, rifampin, ethambutol, streptomycin and pyrazinamide).

A "multi-drug resistant" *M. tuberculosis* infection refers to a *M. tuberculosis* infection wherein the infecting strain is resistant to two or more of "front-line" chemotherapeutic agents effective in treating a *M. tuberculosis* infection.

A "chemotherapeutic agent effective in treating a *M. tuberculosis* infection" refers to pharmacological agents known and used in the art to treatM tuberculosis infections. Exemplified pharmacological agents used to treat *M. tuberculosis* infections include, but are not limited to amikacin, aminosalicylic acid, capreomycin, cycloserine, ethambutol, ethionamide, isoniazid, kanamycin, pyrazinamide, rifamycins (i.e., rifampin, rifapentine and rifabutin), streptomycin, ofloxacin, ciprofloxacin, clarithromycin, azithromycin and fluoroquinolones. "First-line" chemotherapeutic agents used to treat a *M. tuberculosis* infection that is not drug resistant include isoniazid, rifampin, ethambutol, streptomycin and pyrazinamide. "Second-line" chemotherapeutic agents used to treat a *M. tuberculosis* infection that has demonstrated drug resistance to one or more "first-line" drugs include ofloxacin, ciprofloxacin, ethionamide, aminosalicylic acid, cycloserine, amikacin, kanamycin and capreomycin. Such pharmacological agents are reviewed in Chapter 48 of *Goodman and Gilman's The Pharmacological Basis of Therapeutics*, Hardman and Limbird eds., 2001.

"FL" refers to full-length, i.e., a polypeptide that is the same length as the wild-type polypeptide.

"His tag" refers to a string of His residues, typically 6 residues that are inserted at the N-terminus, usually immediately after the initiating Met residue or else at the C-terminus. They are usually heterologous to the native sequence but are incorporated since they facilitate isolation by improving the protein binding to immobilised metal affinity chromatography resins (IMAC). Generally speaking the presence or absence of a His tag is not of significance from the point of view of causing a useful immune response against the antigenic protein to be elicited. In case an adverse immune reaction against the His tag itself is elicited it is considered best to minimize the length of the His tag eg to 4 or less residues, in particular two residues.

The term "immunogenic fragment thereof" refers to a polypeptide comprising an epitope that is recognized by cytotoxic T lymphocytes, helper T lymphocytes or B cells. Typically an immunogenic fragment of Mtb72f will be a polypeptide containing 500 or more amino acids eg 600 or more amino acids eg 700 or more amino acids. The invention also embraces a plurality of fragments eg overlapping fragments which together cover all or substantially all (eg 500 or more amino acids eg 600 or more amino acids eg 700 or more amino acids) of the sequence of a Mtb72F fusion protein.

The term "*Mycobacterium* species of the tuberculosis complex" includes those species traditionally considered as causing the disease tuberculosis, as well as *Mycobacterium* environmental and opportunistic species that cause tuberculosis and lung disease in immune compromised patients, such as patients with AIDS, e.g., *M. tuberculosis, M. bovis,* or *M. africanum,* BCG, *M. avium, M. intracellulare, M. celatum, M. genavense, M. haemophilum, M. kansasii, M. simiae, M. vaccae, M. fortuitum,* and *M. scrofulaceum* (see, e.g., Harrison's Principles of Internal Medicine, Chapter 150, pp. 953-966 (16th ed., Braunwald, et al., eds., 2005).

An adjuvant refers to the components in a vaccine or therapeutic composition that increase the specific immune response to the antigen (see, e.g., Edelman, *AIDS Res. Hum Retroviruses* 8:1409-1411 (1992)). Adjuvants induce immune responses of the Th1-type and Th-2 type response. Th1-type cytokines (e.g., IFN-γ, IL-2, and IL-12) tend to favor the induction of cell-mediated immune response to an administered antigen, while Th-2 type cytokines (e.g., IL-4, IL-5, Il-6, IL-10 and TNF-β) tend to favor the induction of humoral immune responses. Adjuvants capable of preferential stimulation of a Th-1 cell-mediated immune response are described in WO 94/00153 and WO 95/17209.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Fusion polypeptide" or "fusion protein" refers to a protein having at least two heterologous *Mycobacterium* sp. polypeptides covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, subsequences, and interspecies homologs of the antigens that make up the fusion protein. *Mycobacterium tuberculosis* antigens are described in Cole et al., Nature 393:537 (1998), which discloses the entire *Mycobacterium tuberculosis* genome. The complete sequence of *Mycobacterium tuberculosis* can also be found at www.sanger.ac.uk and at www.pasteur.fr/mycdb/(MycDB). Antigens from other *Mycobacterium* species that correspond to *M. tuberculosis* antigens can be identified, e.g., using sequence comparison algorithms, as described herein, or other methods known to those of skill in the art, e.g., hybridization assays and antibody binding assays.

Exemplary Mtb72f fusion proteins of use in the present invention include:

Proteins comprising residues 8-729 of the sequence of SEQ ID No: 2;

Proteins comprising or consisting of the sequence of SEQ ID No: 2 (Mtb72F) optionally without the His tag forming residues 2-7 of said sequence or with a His tag of different length;

Fusion proteins comprising the sequence of SEQ ID No: 2 optionally without the His tag forming residues 2-7 of said sequence or with a His tag of different length (e.g. a protein comprising residues 8-729 of the sequence of SEQ ID No: 2) together with one or more *M. tuberculosis* antigens, for example one or more of the proteins listed above, or an immunogenic fragment of any of them;

Proteins comprising residues 4-725 of the sequence of SEQ ID No: 4 (Mtb72F);

Proteins comprising or consisting of the sequence of SEQ ID No: 4 (Mtb72F) optionally without the His tag forming residues 2-3 of said sequence or with a His tag of different length;

and fusion proteins comprising the sequence of SEQ ID No: 4 optionally without the His tag forming residues 2-3 of said sequence or with a His tag of different length (e.g. a protein comprising residues 4-725 of the sequence of SEQ ID No: 4) together with one or more *M. tuberculosis* antigens, for example one or more of the proteins listed above, or an immunogenic fragment of any of them;

Exemplary immunogenic fragments of a Mtb72f fusion proteins of use in the present invention include:

Proteins comprising or consisting of the sequence of TbH9-Ra35 (Mtb59F); or TbH9; or Ra35; or Ra12; and fusion proteins comprising said sequences together with one or more *M. tuberculosis* antigens, for example one or more of the proteins listed above, or an immunogenic fragment of any of them.

Further exemplary immunogenic fragments of a Mtb72f fusion proteins of use in the present invention include:

Proteins comprising or consisting of the sequence of TbH9-Ra35 (Mtb59F) or Ra35 in which the position corresponding to Ser710 in SEQ ID No: 2 has been changed to Ala; and Fusion proteins comprising said sequences together with one or more *M. tuberculosis* antigens, for example one or more of the proteins listed above, or an immunogenic fragment of any of them.

More specifically the Mtb72f is:

a polypeptide comprising residues 8-729 of SEQ ID NO:2; or a polypeptide consisting of residues 1 and 8-729 of SEQ ID NO:2 optionally with a His tag inserted following the initial Met residue; or a polypeptide of SEQ ID NO:2; or a polypeptide comprising residues 4-725 of SEQ ID NO:4; or a polypeptide consisting of residues 1 and 4-725 of SEQ ID NO:4 optionally with a His tag inserted following the initial Met residue.; or a polypeptide of SEQ ID NO:4; or a polypeptide of SEQ ID NO:6.

Further exemplary Mtb72f fusion proteins and immunogenic fragments thereof include the proteins mentioned above in which the N- and/or the C-terminus have been shortened by e.g. 5 or 4 or 3 or 2 or 1 amino acid residues.

Further exemplary Mtb72f fusion proteins and immunogenic fragments thereof include the proteins mentioned above in which up to 10% of the amino acids, e.g. up to 5% of the amino acids (eg up 10 e.g. up to 5) amino acids have been replaced with conservative substitutions as defined herein.

Exemplary Mtb72f nucleic acids of use in the present invention include nucleic acids (e.g. DNA molecules) encoding the aforementioned exemplary Mtb72f fusion proteins and immunogenic fragments thereof. One set of specific DNA molecules that may be mentioned comprise nucleotides 63-2228 of SEQ ID No: 1. Another set of specific DNA molecules that may be mentioned comprise nucleotides 10-2175 of SEQ ID No: 3. Specific DNA molecules that may be mentioned comprise or consist of SEQ ID No: 1 or SEQ ID No: 3 or SEQ ID No: 5.

The term "fused" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)′$_2$, a dimer of Fab which itself is a light chain joined to $V_H$-$C_H$1 by a disulfide bond. The F(ab)′$_2$ may be reduced under mild conditions to break the disulfide linkage in the hinge region, thereby converting the F(ab)′$_2$ dimer into an Fab′ monomer. The Fab′ monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 inMonoclonal Antibodies and Cancer Therapy (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, *A Laboratory Manual* (1988) and *Using Antibodies: A Laboratory Manual* (1998), for a description of immunoassay formats and conditions that can be used to determine specific immunoreactivity). Typically a specific or selective reaction will be at least twice background signal or noise and more typically more than 10 to 100 times background.

Polynucleotides may comprise a native sequence (i.e., an endogenous sequence that encodes an individual antigen or a portion thereof) or may comprise a variant of such a sequence. Polynucleotide variants may contain one or more substitutions, additions, deletions and/or insertions such that the biological activity of the encoded fusion polypeptide is not diminished, relative to a fusion polypeptide comprising native antigens. Variants preferably exhibit at least about 70% identity, more preferably at least about 80% identity and most preferably at least about 90% identity to a polynucleotide sequence that encodes a native polypeptide or a portion thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 25 to 500, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes aMycobacterium antigen or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection.

Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotide Identification and Characterization

Polynucleotides may be identified, prepared and/or manipulated using any of a variety of well established techniques. For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., *Proc. Natl. Acad. Sci. USA* 93:10614-10619 (1996) and Heller et al., *Proc. Natl. Acad. Sci. USA* 94:2150-2155 (1997)). Alternatively, polynucleotides may be amplified from cDNA prepared from cells expressing the proteins described herein, such as *M. tuberculosis* cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., a *M. tuberculosis* cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual* (2000)). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then be assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186 (1988)), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19 (1991)) and walking PCR (Parker et al., *Nucl. Acids. Res.* 19:3055-60 (1991)). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al., *Nucl. Acids Res. Symp. Ser.* pp. 215-223 (1980), Horn et al., *Nucl. Acids Res. Symp. Ser.* pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., *Science* 269:202-204 (1995)) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, *Proteins, Structures and Molecular Principles* (1983)) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (2000), and Ausubel et al., *Current Protocols in Molecular Biology* (updated annually).

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; piN vectors (Van Heeke & Schuster, *J. Biol. Chem.* 264:5503-5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in *McGraw Hill Yearbook of Science and Technology* pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells. Methods and protocols for working with adenovirus vectors are reviewed in Wold, *Adenovirus Methods and Protocols,* 1998. Additional references regarding use of adenovirus vectors can be found in *Adenovirus: A Medical Dictionary, Bibliography, and Annotated Research Guide to Internet References,* 2004.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-32 (1977)) and adenine phosphoribosyltransferase (Lowy et al., *Cell* 22:817-23 (1990)) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath et al., *Prot. Exp. Purif* 3:263-281 (1992) while the enterokinase cleavage site provides a means for purifying the desired polypeptide from the fusion protein. A discussion of vectors which contain fusion proteins is provided in Kroll et al., *DNA Cell Biol.* 12:441-453 (1993)).

In addition to recombinant production methods, polypeptides of the invention, and fragments thereof, may be produced by direct peptide synthesis using solid-phase techniques (Merrifield, *J Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome, the current adenovirus vectors, with the help of 293 cells, carry foreign DNA in either the E1, the D3 or both regions. In nature, adenovirus can package approximately 105% of the wild-type genome, providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently improved methods for culturing 293 cells and propagating adenovirus were disclosed. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus, demonstrating their safety and therapeutic potential as in vivo gene transfer vectors.

Adenovirus vectors have been used in eukaryotic gene expression and vaccine development. Recently, animal studies suggested that recombinant adenovirus could be used for gene therapy. Studies in administering recombinant adenovirus to different tissues include trachea instillation, muscle injection, peripheral intravenous injections and stereotactic inoculation into the brain.

Adenovirs vectors may originate from human adenovirus. Alternatively they may originate from adenovirus of other species eg chimpanzee which may have the advantage that the viral vectors are not neutralized by antibodies against human adenovirus circulating in many human subjects.

2. Retroviruses

The retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome.

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression require the division of host cells.

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin. Using antibodies against major histocompatibility complex class I and class II antigens, they demonstrated the infection of a variety of human cells that bore those surface antigens with an ecotropic virus in vitro.

3. Adeno-Associated Viruses

AAV is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter.

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins.

There are several factors that prompted researchers to study the possibility of using rAAV as an expression vector One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus, lentiviruses, polio viruses and herpes viruses may be employed. They offer several attractive features for various mammalian cells.

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome. This suggested that large portions of the genome could be replaced with foreign genetic material. The hepatotropism and persistence (integration) were particularly attractive properties for liver-directed gene transfer. Researchers have introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection.

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. One group successfully injected polyomavirus DNA in the form of calcium phosphate precipitates into liver and spleen of adult and newborn mice demonstrating active viral replication and acute infection. One group also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them. Several devices for accelerating small particles have been developed. One such device relies on a high voltage discharge to generate an electrical current, which in turn provides the motive force. The microprojectiles used have consisted of biologically inert substances such as tungsten or gold beads.

Selected organs including the liver, skin, and muscle tissue of rats and mice have been bombarded in vivo. This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Polypeptide Compositions

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

Immunogenic portions may generally be identified using well known techniques, such as those summarized in Paul, *Fundamental Immunology*, 3rd ed., 243-247 (1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a *Mycobacterium* sp. protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow & Lane, *Antibodies: A Laboratory Manual* (1988) and *Using Antibodies: A Laboratory Manual* (1998). For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Polypeptides of the invention, immunogenic fragments thereof, and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146 (1963). Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46 (1985); Murphy et al., *Proc. Natl. Acad. Sci. USA* 83:8258-8262 (1986); U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, e.g., Stoute et al., *New Engl. J. Med.* 336:86-91 (1997)).

Within preferred embodiments, an immunological fusion partner is derived from protein D, a surface protein of the gram-negative bacterium *Haemophilus* influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from *influenzae* virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

T Cells

Immunotherapeutic compositions may also, or alternatively, comprise T cells specific for a *Mycobacterium* antigen. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a polypeptide of the invention, polynucleotide encoding such a polypeptide, and/or an antigen presenting cell (APC) that expresses such a polypeptide. Such stimulation is performed under conditions and for a time sufficient to permit the generation of T cells that are specific for the polypeptide. Preferably, the polypeptide or polynucleotide is present within a delivery vehicle, such as a microsphere, to facilitate the generation of specific T cells.

T cells are considered to be specific for a polypeptide of the invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a polypeptide, polynucleotide or polypeptide-expressing APC may be CD4+ and/or CD8+. Protein-specific T cells may be expanded using standard techniques. Within preferred embodiments, the T cells are derived from a patient, a related donor or an unrelated donor, and are administered to the patient following stimulation and expansion.

For therapeutic purposes, CD4+ or CD8+ T cells that proliferate in response to a polypeptide, polynucleotide or APC can be expanded in number either in vitro or in vivo. Proliferation of such T cells in vitro may be accomplished in a variety of ways. For example, the T cells can be re-exposed to a polypeptide, or a short peptide corresponding to an immunogenic portion of such a polypeptide, with or without the addition of T cell growth factors, such as interleukin-2, and/or stimulator cells that synthesize a polypeptide. Alternatively, one or more T cells that proliferate in the presence of ar protein can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell, antibody, and chemotherapeutic compositions disclosed herein in pharmaceutically-acceptable solutions for administration to a cell or an animal, either alone, or in combination with one or more other modalities of therapy.

It will also be understood that, if desired, the nucleic acid segment (e.g., RNA or DNA) that expresses a polypeptide as disclosed herein may be administered in combination with other agents as well, such as, e.g., other proteins or polypeptides or various pharmaceutically-active agents, including chemotherapeutic agents effective against a *M. tuberculosis* infection. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation. Typically, formulations comprising a therapeutically effective amount deliver about 2 g to about 50 µg Mtb72f polypeptide per administration, more typically about 5 µg to about 40 µg Mtb72f polypeptide per administration.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations usually contain between 2 g to 50 g of Mtb72f polypeptide. Naturally, the amount of active compound(s) in each therapeutically useful composition may be prepared is such a way that a suitable dosage will be obtained in any given unit dose of the compound.

Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal and Buccal Delivery

In certain embodiments, the pharmaceutical compositions may be delivered by intranasal sprays, buccal sprays, inhalation, and/or other aerosol delivery vehicles. Methods for delivering genes, nucleic acids, and peptide compositions directly to the lungs eg via nasal and buccal aerosol sprays has been described e.g., in U.S. Pat. Nos. 5,756,353 and 5,804,212 (each specifically incorporated herein by reference in its entirety). Likewise, the delivery of drugs using intranasal microparticle resins and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (such as the use of liposomes and nanocapsules in the targeted antibiotic therapy for intracellular bacterial infections and diseases). Recently, liposomes were developed with improved serum stability and circulation half-times (U.S. Pat. No. 5,741,516, specifically incorporated herein by reference in its entirety). Further, various methods of liposome and liposome like preparations as potential drug carriers have been reviewed (U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally resistant to transfection by other procedures including T cell suspensions, primary hepatocyte cultures and PC 12 cells. In addition, liposomes are free of the DNA length constraints that are typical of viral-based delivery systems. Liposomes have been used effectively to introduce genes, drugs, radiotherapeutic agents, enzymes, viruses, transcription factors and allosteric effectors into a variety of cultured cell lines and animals. In addition, several successful clinical trails examining the effectiveness of liposome-mediated drug delivery have been completed. Furthermore, several studies suggest that the use of liposomes is not associated with autoimmune responses, toxicity or gonadal localization after systemic delivery.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

The following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention. Such particles may be are easily made, as described (U.S. Pat. No. 5,145,684, specifically incorporated herein by reference in its entirety).

Vaccines

In certain preferred embodiments of the present invention, vaccines are provided. The vaccines will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally known. Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

Illustrative vaccines may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198 (1998), and references cited therein. Appropriate nucleic acid expression systems contain the necessary DNA sequences for expression in the patient (such as a suitable promoter and terminating signal). Bacterial delivery systems involve the administration of a bacterium host cell (for example, a *Mycobacterium, Bacillus* or *Lactobacillus* strain, including *Bacillus*-Calmette-Guerrin or *Lactococcus lactis*) that expresses an immunogenic portion of the polypeptide on its cell surface or secretes such an epitope (see, for example, Ferreira, et al., *An Acad Bras Cienc* (2005) 77:113-124; and Raha, et al., *Appl Microbiol Biotechnol* (2005) PubMedID 15635459). In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321 (1989); Flexner et al., *Ann. N.Y. Acad. Sci.* 569:86-103 (1989); Flexner et al., *Vaccine* 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627 (1988); Rosenfeld et al., *Science* 252:431-434 (1991); Kolls et al., *Proc. Natl. Acad. Sci. USA* 91:215-219 (1994); Kass-Eisler et al., *Proc. Natl. Acad. Sci. USA* 90:11498-11502 (1993); Guzman et al., *Circulation* 88:2838-2848 (1993); and Guzman et al., *Cir. Res.* 73:1202-1207 (1993). Techniques for incorporating DNA into such expression systems are well known to those of ordinary skill in the art. The DNA may also be "naked," as described, for example, in Ulmer et al., *Science* 259:1745-1749 (1993) and reviewed by Cohen, *Science* 259:1691-1692 (1993). The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the vaccine compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, Bordatella pertussis or *Mycobacterium* species or *Mycobacterium* derived proteins. For example, delipidated, deglycolipidated *M. vaccae* ("pVac") can be used. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS01B, AS02A, AS15, AS-2 and derivatives thereof (GlaxoSmithKline, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Janeway, et al., *Immunobiology*, 5$^{th}$ Edition, 2001.

Preferred adjuvants for use in eliciting a predominantly Th1-type response include, for example, a combination of monophosphoryl lipid A, preferably 3-O-deacylated monophosphoryl lipid A (3D-MPL), optionally with an aluminum salt (see, for example, Ribi, et al., 1986, Immunology and Immunopharmacology of Bacterial Endotoxins, Plenum Publ. Corp., NY, pp. 407-419; GB 2122204B; GB 2220211; and U.S. Pat. No. 4,912,094). A preferred form of 3D-MPL is in the form of an emulsion having a small particle size less than 0.2 mm in diameter, and its method of manufacture is disclosed in WO 94/21292. Aqueous formulations comprising monophosphoryl lipid A and a surfactant have been described in WO 98/43670. Exemplified preferred adjuvants include AS01B (MPL and QS21 in a liposome formulation), 3D-MPL and QS21 in a liposome formulation, AS02A (MPL and QS21 and an oil in water emulsion), 3D-MPL and QS21 and an oil in water emulsion, and AS15, available from GlaxoSmithKline. MPL adjuvants are available from GlaxoSmithKline, Seattle, Wash. (see U.S. Pat. Nos. 4,436,727; 4,877,611; 4,866,034 and 4,912,094).

CpG-containing oligonucleotides (in which the CpG dinucleotide is unmethylated) also induce a predominantly Th1 response. CpG is an abbreviation for cytosine-guanosine dinucleotide motifs present in DNA. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). CpG when formulated into vaccines, is generally administered in free solution together with free antigen (WO 96/02555; McCluskie and Davis, supra) or covalently conjugated to an antigen (WO 98/16247), or formulated with a carrier such as aluminium hydroxide ((Hepatitis surface antigen) Davis et al. supra; Brazolot-Millan et al., Proc. Natl. Acad. Sci., USA, 1998, 95(26), 15553-8). CpG is known in the art as being an adjuvant that can be administered by both systemic and mucosal routes (WO 96/02555, EP 468520, Davis et al., *J. Immunol*, 1998, 160(2):870-876; McCluskie and Davis, *J. Immunol.*, 1998, 161(9):4463-6).

Another preferred adjuvant is a saponin or saponin mimetics or derivatives, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210. Additional saponin adjuvants of use in the present invention include QS7 (described in WO 96/33739 and WO 96/11711) and QS17 (described in U.S. Pat. No. 5,057,540 and EP 0 362 279 B1).

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2," SBAS-4, or SBAS6, available from GlaxoSmithKline, Rixensart, Belgium), Detox (Corixa, Hamilton, Mont.), RC-529 (Corixa, Hamilton, Mont.) and other aminoalkyl glucosaminide 4-phosphates (AGPs), such as those described in U.S. Pat. Nos. 6,113,918 and 6,355,257, the disclosures of which are incorporated herein by reference in their entireties.

Further example adjuvants include synthetic MPL and adjuvants based on Shiga toxin B subunit (see WO2005/112991).

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429-1438 (1996)) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly (lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau & Steinman, *Nature* 392:245-251 (1998)) and have been shown to be effective as a physiological adjuvant for eliciting prophylactic or therapeutic antitumor immunity (see Timmerman & Levy, *Ann. Rev. Med.* 50:507-529 (1999)). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600 (1998)).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a protein (or portion or other variant thereof) such that the polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and Cell Biology* 75:456-460 (1997). Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1: Preparation of Mtb72f (no His Tag) (SEQ ID No: 6)

Construction of the Mtb72f Expression Vector

Mtb72f is a fusion protein formed from 2 *Mycobacterium tuberculosis* proteins Mtb32 and Mtb39. Mtb72f is constructed by fusing Mtb39 and the N and C terminal portions of Mtb32 as follows: Mtb32 C-terminal end-Mtb39-Mtb32 N-terminal end. Specifically, Mtb72f protein was generated by the sequential linkage in tandem of the open reading frames (ORFs) encoding the ~14-kDa C-terminal fragment of Mtb32 (residues 192-323; 132 amino acids) to the full length ORF of Mtb39 followed at the C-terminus with the ~20-kDa N-terminal portion (residues 1-195) of Mtb32. This was accomplished by using sequence-specific oligonucleotides containing unique restriction sites (EcoRI and EcoRV) and devoid of the stop codons at the C-terminal ends (in the case of Mtb32-C and Mtb39) for polymerase chain reaction (PCR) off of genomic DNA from the *M. tuberculosis* strain H37Rv.

The details of the process are as follows:

First, the DNA encoding the C-terminal portion of Mtb32 (Mtb32C) was cloned from H37Rv using PCR with the following oligonucleotides: 5' (5'-CAA-TTA-CAT-ATG-CAT-CAC-CAT-CAC-CAT-CAC-ACG-GCC-GCG-TCC-GAT-AAC-TTC-3'; SEQ ID NO:7) and 3' (5'-CTA-ATC-GAA-TCC-GGC-CGG-GGG-TCC-CTC-GGC-CAA-3'; SEQ ID NO:8). The 5' oligonucleotide contained an NdeI restriction site (underlined) encompassing the ATG initiation codon. The 3' oligonucleotide contained an EcoRI restriction site (underlined). These oligonucleotides were used to amplify Mtb32C, a 396 nucleotide portion of Mtb32 and the resulting product was subcloned into the NdeI and EcoRI sites of an expression vector. Digesting with EcoRI and EcoRV subsequently linearized the Mtb32C plasmid. For Mtb39, the following oligonucleotides were used for PCR amplification and cloning: 5'-(5'-CTA-ATC-GAA-TTC-ATG-GTG-GAT-TTC-GGG-GCG-TTA-3'; SEQ ID NO:9) and 3' (5'-CTA-ATC-GAT-ATC-GCC-GGC-TGC-CGG-AGA-ATG-CGG-3'; SEQ ID NO: 10). The 5' oligonucleotide contained an EcoRI restriction site (underlined) while the 3' oligonucleotide contained an EcoRV restriction site (underlined). The full-length coding sequence of Mtb39 was amplified, digested, and sub-cloned in-frame downstream of Mtb32c using the predigested plasmid from the first step.

The 5' and 3' oligonucleotides of the N-terminal fragment of Mtb32 were designed as follows: 5'-(5'-CTA-ATC-GAT-ATC-GCC-CCG-CCG-GCC-TTG-TCG-CAG-GAC-3'; SEQ ID NO: 11) and 3' (5'-CTA-ATC-GAT-ATC-CTA-GGA-CGC-GGC-CGT-GTT-CAT-AC-3'; SEQ ID NO: 12). Both sets of oligonucleotides contained an EcoRV restriction site (underlined) while the 3' oligonucleotide also included a stop codon (italics). The oligonucleotides were designed to amplify a 585 bp portion of Mtb32 encoding the predicted N-terminal domain of this protein. The resulting PCR product was sub-cloned into the Mtb32c-Mtb39 fusion plasmid. The proper orientation of inserts and the absence of mutations was then verified by DNA sequencing.

For the final construct, used for making the Master Cell Bank and Manufacturer's Working Cell Bank, the 6xHis affinity tag was removed by PCR and the open reading frame (ORF) for Mtb72f was subcloned into pPDM, a pET derived expression vector. The ORF codes for a polyprotein of about 72 kDa (Mtb72f), with domains organized in the linear order: Mtb32C-Mtb39-Mtb32N. This DNA was then transformed into the HMS174 pLysS strain of *E. coli* and used for testing, cell banking, and manufacture.

Production of Mtb72f Bulk Drug Substance

The manufacturing process for the production of Mtb72f is summarized as follows:

Fermentation followed by cell harvest by centrifugation, cell disruption (microfluidizer) and centrifugation to yield an inclusion body pellet;

Purification of the inclusion body pellet by extraction in 8M urea, followed by Q Sepharose Fast Flow (QFF) chromatography, Ceramic Hydroxyapatite (CHT) chromatography, diafiltration, and sterilizing filtration to yield the purified bulk drug substance.

Fermentation

Fermentations are performed at a 10 L working volume. The fermentor is inoculated with 300 mL of a shake flask culture of the working seed cells grown at 37° C. overnight. Both the inoculum and the fermentation use a semidefined medium with plant-derived glycerol as the primary carbon source. The composition of the medium is shown in the table below. All medium components are sterilized by heating at 121° C. for 20 minutes or by sterilizing filtration. During the fermentation the fermentor is maintained at a temperature of 37° C. Air is sparged at a rate of 5 standard liters per minute (SLPM). The pH of the medium is maintained at 7.0 by automatic addition of acid ($H_2SO_4$) or base (NaOH). The fermentor is programmed to control the dissolved oxygen at 30% by automatically adjusting the agitation, while maintaining a minimum agitation of 200 rpm. Foam control within the fermentor is achieved by the automatic addition of 1.05% SAG-471 silicone antifoam (Witco Corp.). When the cell density reaches an optical density (600 nm) of approximately 3.5, isopropyl-beta-D-thiogalactopyranoside (IPTG) is added to the fermentor to a concentration of 1.0 mM. The IPTG induces expression of the recombinant gene encoding the Mtb72f protein. At 3.0 hours post-induction, the fermentor is cooled and the cells are harvested by centrifugation in 1 L centrifuge bottles.

Composition of Fermentation Medium

| Material | Concentration |
| --- | --- |
| Yeast Extract | 15 g/L |
| Glycerol | 30 g/L |
| Magnesium sulfate, heptahydrate ($MgSO_4$—) | 0.5 g/L |
| Potassium phosphate, monobasic ($KH_2PO_4$) | 2.4 g/L |
| Sodium phosphate, dibasic ($Na_2HPO_4$) | 3.2 g/L |
| Ammonium chloride (NH4Cl) | 1.0 g/L |
| Sodium chloride (NaCl) | 0.5 g/L |
| Kanamycin sulphate | 30 mg/L |
| Chloramphenicol | 34 mg/L |
| SAG-471 silicone antifoam (Witco Corp.) | 0.0005% (v/v) (not included in |

Isolation of Inclusion Bodies

The cell pellets are resuspended and pooled in 2.3 L of lysis Buffer (50 mM NaCl, 10 mM Tris pH 8.0), and a M-1 10Y Microfluidizer is used to disrupt the cells. The cells are passed through the Microfluidizer five times at a pressure of 11,000±1,000 psi. The suspension is centrifuged at 8000×g in 500 mL bottles. Under these conditions, the inclusion bodies (IB) containing the Mtb72f protein are pelleted, while most of the cell debris remains in the supernatant. The IB pellets are resuspended in Wash Buffer (2 M urea, 50 mM NaCl, 10 mM Tris pH 8.0), followed by centrifugation at 8,000 g. The supernatant fractions are discarded and the IB pellets are stored at −70° C. to −80° C. until needed for further purification.

Purification of Polyprotein

The frozen IB preparations are thawed at 37° C. for 15 minutes and then resuspended in 8 M urea, 50 mM NaCl, 20 mM Bis-tris propane, pH 7.0 (Buffer A) using gentle mechanical agitation. The resuspended IBs are then stirred at room temperature with a magnetic stir bar at 300 rpm for 2 hrs. The IB extract is then centrifuged at high speed and the resultant supernatant fraction is filtered through a 0.45 uM filter (Pall, Supor) prior to chromatographic fractionation.

The IB extract is applied to a column containing Q Sepharose Fast Flow (QFF) anion exchange resin (10×12.5 cm Amersham/Pharmacia BPG; 1 L packed bed) previously sanitized with 1 N NaOH and then equilibrated with Buffer A. The column is developed at a linear flow rate of 60 cm/hr with Buffer A and the flow-through containing predominantly lower mass contaminants is collected for reference. The bulk of the Mtb72f is eluted in a single step using 8 M urea, 90 mM NaCl, 20 mM Bis-tris propane, pH 7.0 and is collected as a single bulk peak based on absorbance.

QFF resins are highly cross-linked agarose resins with a quaternary amine functional group that is positively charged in the conditions used during purification. The charged matrix allows for the binding of various anions that can then be selectively eluted using a salt gradient. This anion exchange chromatography is used to separate nucleic acids and endotoxin, which bind tightly to the resin, from the protein, which is bound more weakly and elutes prior to these contaminants. Additionally, this step removes uncharged contaminants and a large part of the protein impurities.

The 90 mM NaCl eluate peak is from the QFF column is applied to a column (2.6×12 cm Amersham/Pharmacia XK26/20; 63 mL packed bed) containing MacroPrep® ceramic hydroxyapatite (CHT) (type I, 40 uM, BioRad) previously sanitized using 1 N NaOH and then equilibrated with Buffer C (8 M urea, 250 mM NaCl, and 20 mM Bis-tris propane, pH 7.0). The flow-through material (FT1) containing the majority of the Mtb72f, free of contaminants, is collected. The column is washed with Buffer C and any resultant UV-absorbing material is collected. Finally, the column is eluted in Buffer D (8 M urea, 200 mM sodium phosphate, pH 7.4).

MacroPrep® CHT is a spherical, macroporous form of hydroxyapatite $[Ca_5(PO_4)_3OH]2$. CHT chromatography can be a highly selective method of purification if the proper binding and elution conditions are found. The modes of binding include ion exchange type binding to charged calcium and phosphate ions as well as chelation of molecules. DNA will bind to this resin and high selectivity for individual proteins can be achieved. The conditions used for the purification of Mtb72f serve as a polishing step allowing virtually complete removal of detectable host cell contaminants.

During chromatographic separations, ultraviolet (UV) absorbance, conductivity, pressure, pH, flow-rate, and ambient temperature are monitored and recorded. The initial CHT flow-through material (FT1) is used for further downstream processing.

Diafiltration and Sterile Filtration

Diafiltration is performed on the CHT FT1 pool to remove the urea and replace the buffer with 20 mM Tris pH 7.5. The diafiltration is performed using a Pall Minim™ system with an LV-Centramate™ tangential flow filtration device with a 30 kDa molecular weight cutoff (MWCO) ultrafiltration membrane. The Mtb72f solution in 20 mM Tris pH 7.5 is filter sterilized using a 0.2-um sterilizing filter (Millipak 40). Fifty mL of the solution are distributed into sterile 60 mL PETG (polyethylene terephthalate copolymer) media bottles, then frozen and stored at −70° C. This material is the Mtb72f purified bulk drug substance.

Example 2: Preparation of Mtb72f (6 His Tag) (SEQ ID No: 2)

The method of Example 1 may be followed, except that the step of subcloning into pPDM in order to remove the His Tag is omitted.

Example 3: Preparation of M72 (2 His Tag) (SEQ ID No: 4)

Construction of the M72 Expression Vector

Starting material for the construction of M72 antigen was the recombinant plasmid 6His-Mtb72fmut. 6His-Mtb72fmut was prepared by site-directed mutagenesis using the 6his-Mtb72f recombinant plasmid (see Example 1) as template. Site-directed mutagenesis involved replacing the codon for Ser at position 710 in SEQ ID No: 1 with a codon for Ala. The deletion of four N-terminal histidines present on the 6His-Mtb72fmut construct (Corixa plasmid) was achieved with "Gene Tailor Site-Directed Mutagenesis System" (Invitrogen), leading to the expected 2His-Mtb72Fmut construct. After sequence verification, 2His-Mtb72fmut coding sequence was excized from the plasmid (by enzymatic restriction), gel purified and ligated into pET29a expression vector resulting in the final recombinant plasmid pET29a/2His-Mtb72fmut. After sequence verification the recombinant plasmid was given the official designation pRIT15497 and used to transform HMS174(DE3) host cells. pRIT15497 codes for a 725 amino-acid protein named M72.

Production of M72 Protein

The same production process as described for Mtb72f (see Example 1) may be employed., except that for M72 production, chloramphenicol is absent in the fermentation medium.

Biological Example 1: A Mouse Model of an Inactive/Latent State of *M. tuberculosis* Infection To establish a mouse model of latent *M. tuberculosis* infection, the SWR strain was used.

SWR mice are not immunocompromised, but are deficient for secretion of complement component C5 (see, Ooi and Colten, *Nature* (1979) 282:207-8). SWR mice are incapable of establishing a chronic state of Mtb infection, but develop diffuse granulomatous pneumonia characterized by large epitheloid and foamy macrophages with crystalloid inclusions (neutrophil or eosinophil-derived granules that have been phagocytosed), multifocal necrosis, neutrophil accumulation and scant lymphocytes (see, Turner, et al., *J Submicrosc Cytol Pathol*. (2001) 33(1-2):217-9; and Turner, et al., *Infect Immun*. (2003) 71(9):5266-72). Following is the protocol for using the Swiss Webster (SWR/J) mouse strain in a model of latent *M. tuberculosis* infection to evaluate the therapeutic efficacy of Mtb72f (SEQ ID No:6) formulated with AS01B adjuvant. Double strength AS01B is prepared by adding QS21 (5 g) to small unilamellar vesicles (SUV) of dioleoyl phosphatidylcholine (100 μg) containing cholesterol (25 μg) (WO 96/33739) and monophosphoryl lipid A (MPL) (5 μg) in the membrane (see, U.S. Patent Publication No. 2003/0143240). An aliquot for injection (50 l) is prepared by mixing 4 µg of protein in buffer (PBS pH 6.8) with 50 µl of double strength AS01B. Each mouse received two injections of 50 µl (i.e. 8 µg of protein).

A representative timeline for establishing a model of a latent *M. tuberculosis* infection is schematically depicted in FIG. 1.

Day 1: Infect via aerosol with 50-100 colony forming units (CFU) *M. tuberculosis* organisms Day 30-90: Treat a subset of mice with 50 mg rifampin/85 mg isoniazide per Liter of drinking water Day 61: All mice receiving the candidate vaccine 5 should be immunized with rMtb72f+AS01B Day 82: All mice receiving the candidate vaccine should be immunized with rMtb72f+AS01B Day 103: All mice receiving the candidate vaccine should be immunized with rMtb72f+AS01B Day 113: Bleed for IgG assays Various Timepoints: Take Spleens and Lungs for CFU Enumeration & Immunogenicity Variation 1→Treat with chemotherapy for 60 days. Starting at day 30→Rest for 3, 4, 5 months→*CFU in 2 mice at each time point and leave 4-7 mice for survival studies Variation 2→Treat with chemotherapy for 90 days. Starting at day 30→Rest for 4, 5 months→*CFU in 2 mice at each time point and leave 7 mice for survival studies Variation 3→Rest for 4, 5, 6 months→*CFU in 2 mice at each time point and leave 4 mice for survival studies Variation 4→Treat with chemotherapy for 60 days. Starting at day 30→3 immunizations with r72F+AS01B intramuscularly (i.m.) starting at Day 60→Rest for 3, 4, 5 months→*CFU in 2 mice at each time point and leave 4-7 mice for survival studies Variation 5→Treat with chemotherapy for 90 days. Starting at day 30→3 immunizations with r72F+AS01B i.m starting at Day 60→Rest for 4, 5 months→*CFU in 2 mice at each time point and leave 4-7 mice for survival studies Analysis of post-infection antibody responses using rMtb72f to coat the ELISA plates revealed that those groups that received a combination of chemotherapy and Mtb72f+AS01B immunization had a higher antibody response (OD up to 2.0) than mice that were untreated or received chemotherapy treatment alone (OD of less than 0.5) (FIG. 2). Mice immunized with Mtb72f mounted a sizeable Mtb72f-specific antibody response (OD of between 1.5 and 2.5) whether they received 60 or 90 days of chemotherapy (FIG. 3).

Spleen cells were harvested from mice at various intervals after the mice were infected with *M. tuberculosis*. The splenocytes were re-stimulated in vitro with recombinant antigens to measure IFN-γ secretion. IFN-γ levels produced by these cells were uniformly negligible in groups 1 (untreated) and 2 (chemotherapy only) at day 60, with the exception of Mtb39. Positive control stimulations with conA, PPD and BCG lysate demonstrated the cells were capable of synthesizing and secreting IFN-γ in response to other stimulatory molecules (FIG. 4). IFN-γ levels were high in groups receiving Mtb72f+AS01B, but they were low or negligible in groups that had not been immunized with Mtb72f+AS01B, whether or not they had received chemotherapy (FIG. 5).

During the course of tuberculosis infection and subsequent treatment, specific T cells respond. Using intracellular cytokine staining for IFN-γ the percentage of specific $CD4^+$ cell responses to Mtb72F was measured (FIG. 6). There seemed to be no change in the Mtb72F specific $CD4^+$ IFN $\gamma^+$ T cell responses during the course of chemotherapy alone at any time point as measured by this assay (FIG. 7). At day 120 post Mtb infection, the trend of $CD4^+$ $IFN\gamma^+$ response to Mtb72F in groups receiving the Mtb72f plus AS01B vaccine, appeared to increase with the length of time on chemotherapy (FIG. 7).

The results of our experiments demonstrate that SWR mice are susceptible to infection with *M. tuberculosis*. If left untreated, SWR mice die by 115 days post Mtb infection (FIGS. 8 and 9). Mean survival time for mice receiving 60 days of combination chemotherapy was 170 days (FIGS. 8 and 9). Mean survival time for mice receiving 60 days of combination chemotherapy and 3 immunizations of Mtb72f/AS01B was 215 days (FIGS. 8 and 9). Survival for the group of mice receiving chemotherapy is significantly different (95% confidence interval (p=0.0067) from those receiving chemotherapy and the Mtb72f/AS01B vaccine.

We claim:

1. A method of producing a polypeptide comprising the amino acid sequence of SEQ ID NO: 4, the method comprising:
   (a) transforming or transfecting a host cell with an expression vector containing DNA encoding the polypeptide; and
   (b) culturing the host cell under conditions suitable for the expression of the polypeptide from the host cell.

2. The method of claim 1, wherein the host cell is selected from the group consisting of a bacterial cell, a yeast cell, an insect cell, and an animal cell.

3. The method of claim 2, wherein the bacterial host cell is *E. coli*.

4. The method of claim 3, wherein the *E. coli* host cell is the HMS174 pLysS strain of *E. coli*.

5. The method of claim 2, wherein the host cell is a yeast cell.

6. The method of claim 2, wherein the animal host cell is a mammalian host cell.

7. The method of claim 6, wherein the mammalian host cell is selected from COS cell line, and CHO cell line.

8. The method of claim 1, further comprising the step of purifying the polypeptide from the cell culture.

9. The method of claim 8, wherein the step of purifying the polypeptide comprises at least one method selected from the group consisting of anion exchange chromatography, hydroxyapatite chromatography, diafiltration, and sterilizing filtration.

10. A method of producing a polypeptide comprising the amino acid sequence of SEQ ID NO: 4, the method comprising:
    (a) transforming an *E. coli* host cell with an expression vector encoding the polypeptide;
    (b) fermenting the transformed *E. coli* host cell of step (a) in a cell culture under conditions suitable for the expression of the protein from the *E. coli* host cell;
    (c) harvesting the fermented *E. coli* host cell of step (b) by centrifugation of the cell culture;
    (d) disrupting the harvested *E. coli* host cell of step (c);
    (e) centrifuging the disrupted *E. coli* host cell of step (d) to produce an inclusion body pellet;
    (f) extracting the inclusion body pellet of step (e) in a buffer comprising urea; and
    (g) purifying the extracted inclusion body pellet of step (f) by anion exchange chromatography, hydroxyapatite chromatography, diafiltration, and sterilizing filtration.

* * * * *

SEQUENCE LISTING

<160> NUMBER OF SEQ ID NOS: 12

<210> SEQ ID NO 1
<211> LENGTH: 2287
<212> TYPE: DNA
<213> ORGANISM: Artificial Sequence
<220> FEATURE:
<223> OTHER INFORMATION: Tri-fusion protein Mtb72F (Ral2-TbH9-Ra35 or Mtb32-Mtb39)
<220> FEATURE:
<221> NAME/KEY: misc_feature
<222> LOCATION: 30, 33, 2270
<223> OTHER INFORMATION: n = A,T,C or G
<220> FEATURE:
<221> NAME/KEY: CDS
<222> LOCATION: (42)...(2228)

<400> SEQUENCE: 1
tctagaaata attttgttta ctttaagaan ganatataca t atg cat cac cat cac 56
Met His His His His
1 5 cat cac acg gcc gcg tcc gat aac ttc cag ctg tcc cag ggt ggg cag 104
His His Thr Ala Ala Ser Asp Asn Phe Gln Leu Ser Gln Gly Gly Gln
10 15 20

-continued

```
gga ttc gcc att ccg atc ggg cag gcg atg gcg atc gcg ggc cag atc        152
Gly Phe Ala Ile Pro Ile Gly Gln Ala Met Ala Ile Ala Gly Gln Ile
             25                  30                  35 cga tcg ggt ggg ggg tca ccc acc gtt cat atc ggg cct acc gcc ttc        200
Arg Ser Gly Gly Gly Ser Pro Thr Val His Ile Gly Pro Thr Ala Phe
         40                  45                  50 ctc ggc ttg ggt gtt gtc gac aac aac ggc aac ggc gca cga gtc caa        248
Leu Gly Leu Gly Val Val Asp Asn Asn Gly Asn Gly Ala Arg Val Gln
     55                  60                  65 cgc gtg gtc ggg agc gct ccg gcg gca agt ctc ggc atc tcc acc ggc        296
Arg Val Val Gly Ser Ala Pro Ala Ala Ser Leu Gly Ile Ser Thr Gly
 70                  75                  80                  85 gac gtg atc acc gcg gtc gac ggc gct ccg atc aac tcg gcc acc gcg        344
Asp Val Ile Thr Ala Val Asp Gly Ala Pro Ile Asn Ser Ala Thr Ala
                 90                  95                 100 atg gcg gac gcg ctt aac ggg cat cat ccc ggt gac gtc atc tcg gtg        392
Met Ala Asp Ala Leu Asn Gly His His Pro Gly Asp Val Ile Ser Val
             105                 110                 115 acc tgg caa acc aag tcg ggc ggc acg cgt aca ggg aac gtg aca ttg        440
Thr Trp Gln Thr Lys Ser Gly Gly Thr Arg Thr Gly Asn Val Thr Leu
         120                 125                 130 gcc gag gga ccc ccg gcc gaa ttc atg gtg gat ttc ggg gcg tta cca        488
Ala Glu Gly Pro Pro Ala Glu Phe Met Val Asp Phe Gly Ala Leu Pro
     135                 140                 145 ccg gag atc aac tcc gcg agg atg tac gcc ggc ccg ggt tcg gcc tcg        536
Pro Glu Ile Asn Ser Ala Arg Met Tyr Ala Gly Pro Gly Ser Ala Ser
150                 155                 160                 165 ctg gtg gcc gcg gct cag atg tgg gac agc gtg gcg agt gac ctg ttt        584
Leu Val Ala Ala Ala Gln Met Trp Asp Ser Val Ala Ser Asp Leu Phe
                 170                 175                 180 tcg gcc gcg tcg gcg ttt cag tcg gtg gtc tgg ggt ctg acg gtg ggg        632
Ser Ala Ala Ser Ala Phe Gln Ser Val Val Trp Gly Leu Thr Val Gly
             185                 190                 195 tcg tgg ata ggt tcg tcg gcg ggt ctg atg gtg gcg gcg gcc tcg ccg        680
Ser Trp Ile Gly Ser Ser Ala Gly Leu Met Val Ala Ala Ala Ser Pro
         200                 205                 210 tat gtg gcg tgg atg agc gtc acc gcg ggg cag gcc gag ctg acc gcc        728
Tyr Val Ala Trp Met Ser Val Thr Ala Gly Gln Ala Glu Leu Thr Ala
215                 220                 225 gcc cag gtc cgg gtt gct gcg gcg gcc tac gag acg gcg tat ggg ctg        776
Ala Gln Val Arg Val Ala Ala Ala Ala Tyr Glu Thr Ala Tyr Gly Leu
230                 235                 240                 245 acg gtg ccc ccg ccg gtg atc gcc gag aac cgt gct gaa ctg atg att        824
Thr Val Pro Pro Pro Val Ile Ala Glu Asn Arg Ala Glu Leu Met Ile
                 250                 255                 260 ctg ata gcg acc aac ctc ttg ggg caa aac acc ccg gcg atc gcg gtc        872
Leu Ile Ala Thr Asn Leu Leu Gly Gln Asn Thr Pro Ala Ile Ala Val
             265                 270                 275 aac gag gcc gaa tac ggc gag atg tgg gcc caa gac gcc gcc gcg atg        920
Asn Glu Ala Glu Tyr Gly Glu Met Trp Ala Gln Asp Ala Ala Ala Met
         280                 285                 290 ttt ggc tac gcc gcg gcg acg gcg acg gcg acg gcg acg ttg ctg ccg        968
Phe Gly Tyr Ala Ala Ala Thr Ala Thr Ala Thr Ala Thr Leu Leu Pro
     295                 300                 305 ttc gag gag gcg ccg gag atg acc agc gcg ggt ggg ctc ctc gag cag       1016
Phe Glu Glu Ala Pro Glu Met Thr Ser Ala Gly Gly Leu Leu Glu Gln
310                 315                 320                 325 gcc gcc gcg gtc gag gag gcc tcc gac acc gcg gcg gcg aac cag ttg       1064
Ala Ala Ala Val Glu Glu Ala Ser Asp Thr Ala Ala Ala Asn Gln Leu
```

-continued

|  |  |  |  |  |  |  |  |  |  |  |  |  |  |  |  |
|---|---|---|---|---|---|---|---|---|---|---|---|---|---|---|---|
|  |  | 330 |  |  |  | 335 |  |  |  | 340 |  |  |  |  |  |
| atg | aac | aat | gtg | ccc | cag | gcg | ctg | caa | cag | ctg | gcc | cag | ccc | acg | cag | 1112 |
| Met | Asn | Asn | Val | Pro | Gln | Ala | Leu | Gln | Gln | Leu | Ala | Gln | Pro | Thr | Gln |  |
|  |  | 345 |  |  |  | 350 |  |  |  | 355 |  |  |  |  |  |

| ggc | acc | acg | cct | tct | tcc | aag | ctg | ggt | ggc | ctg | tgg | aag | acg | gtc | tcg | 1160 |
| Gly | Thr | Thr | Pro | Ser | Ser | Lys | Leu | Gly | Gly | Leu | Trp | Lys | Thr | Val | Ser |
|  |  | 360 |  |  |  | 365 |  |  |  | 370 |  |  |  |  |  |

| ccg | cat | cgg | tcg | ccg | atc | agc | aac | atg | gtg | tcg | atg | gcc | aac | aac | cac | 1208 |
| Pro | His | Arg | Ser | Pro | Ile | Ser | Asn | Met | Val | Ser | Met | Ala | Asn | Asn | His |
|  | 375 |  |  |  | 380 |  |  |  | 385 |  |  |  |  |  |  |

| atg | tcg | atg | acc | aac | tcg | ggt | gtg | tcg | atg | acc | aac | acc | ttg | agc | tcg | 1256 |
| Met | Ser | Met | Thr | Asn | Ser | Gly | Val | Ser | Met | Thr | Asn | Thr | Leu | Ser | Ser |
| 390 |  |  |  | 395 |  |  |  | 400 |  |  |  | 405 |  |  |  |

| atg | ttg | aag | ggc | ttt | gct | ccg | gcg | gcg | gcc | cag | gcc | gtg | caa | acc |  | 1304 |
| Met | Leu | Lys | Gly | Phe | Ala | Pro | Ala | Ala | Ala | Gln | Ala | Val | Gln | Thr |  |
|  |  |  | 410 |  |  |  | 415 |  |  |  | 420 |  |  |  |  |

| gcg | gcg | caa | aac | ggg | gtc | cgg | gcg | atg | agc | tcg | ctg | ggc | agc | tcg | ctg | 1352 |
| Ala | Ala | Gln | Asn | Gly | Val | Arg | Ala | Met | Ser | Ser | Leu | Gly | Ser | Ser | Leu |
|  |  | 425 |  |  |  | 430 |  |  |  | 435 |  |  |  |  |  |

| ggt | tct | tcg | ggt | ctg | ggc | ggt | ggg | gtg | gcc | gcc | aac | ttg | ggt | cgg | gcg | 1400 |
| Gly | Ser | Ser | Gly | Leu | Gly | Gly | Gly | Val | Ala | Ala | Asn | Leu | Gly | Arg | Ala |
|  |  | 440 |  |  |  | 445 |  |  |  | 450 |  |  |  |  |  |

| gcc | tcg | gtc | ggt | tcg | ttg | tcg | gtg | ccg | cag | gcc | tgg | gcc | gcg | gcc | aac | 1448 |
| Ala | Ser | Val | Gly | Ser | Leu | Ser | Val | Pro | Gln | Ala | Trp | Ala | Ala | Ala | Asn |
|  | 455 |  |  |  | 460 |  |  |  | 465 |  |  |  |  |  |  |

| cag | gca | gtc | acc | ccg | gcg | gcg | cgg | gcg | ctg | ccg | ctg | acc | agc | ctg | acc | 1496 |
| Gln | Ala | Val | Thr | Pro | Ala | Ala | Arg | Ala | Leu | Pro | Leu | Thr | Ser | Leu | Thr |
| 470 |  |  |  | 475 |  |  |  | 480 |  |  |  | 485 |  |  |  |

| agc | gcc | gcg | gaa | aga | ggg | ccc | ggg | cag | atg | ctg | ggc | ggg | ctg | ccg | gtg | 1544 |
| Ser | Ala | Ala | Glu | Arg | Gly | Pro | Gly | Gln | Met | Leu | Gly | Gly | Leu | Pro | Val |
|  |  |  | 490 |  |  |  | 495 |  |  |  | 500 |  |  |  |  |

| ggg | cag | atg | ggc | gcc | agg | gcc | ggt | ggt | ggg | ctc | agt | ggt | gtg | ctg | cgt | 1592 |
| Gly | Gln | Met | Gly | Ala | Arg | Ala | Gly | Gly | Gly | Leu | Ser | Gly | Val | Leu | Arg |
|  |  | 505 |  |  |  | 510 |  |  |  | 515 |  |  |  |  |  |

| gtt | ccg | ccg | cga | ccc | tat | gtg | atg | ccg | cat | tct | ccg | gca | gcc | ggc | gat | 1640 |
| Val | Pro | Pro | Arg | Pro | Tyr | Val | Met | Pro | His | Ser | Pro | Ala | Ala | Gly | Asp |
|  |  | 520 |  |  |  | 525 |  |  |  | 530 |  |  |  |  |  |

| atc | gcc | ccg | ccg | gcc | ttg | tcg | cag | gac | cgg | ttc | gcc | gac | ttc | ccc | gcg | 1688 |
| Ile | Ala | Pro | Pro | Ala | Leu | Ser | Gln | Asp | Arg | Phe | Ala | Asp | Phe | Pro | Ala |
|  | 535 |  |  |  | 540 |  |  |  | 545 |  |  |  |  |  |  |

| ctg | ccc | ctc | gac | ccg | tcc | gcg | atg | gtc | gcc | caa | gtg | ggg | cca | cag | gtg | 1736 |
| Leu | Pro | Leu | Asp | Pro | Ser | Ala | Met | Val | Ala | Gln | Val | Gly | Pro | Gln | Val |
| 550 |  |  |  | 555 |  |  |  | 560 |  |  |  | 565 |  |  |  |

| gtc | aac | atc | aac | acc | aaa | ctg | ggc | tac | aac | aac | gcc | gtg | ggc | gcc | ggg | 1784 |
| Val | Asn | Ile | Asn | Thr | Lys | Leu | Gly | Tyr | Asn | Asn | Ala | Val | Gly | Ala | Gly |
|  |  |  | 570 |  |  |  | 575 |  |  |  | 580 |  |  |  |  |

| acc | ggc | atc | gtc | atc | gat | ccc | aac | ggt | gtc | gtg | ctg | acc | aac | aac | cac | 1832 |
| Thr | Gly | Ile | Val | Ile | Asp | Pro | Asn | Gly | Val | Val | Leu | Thr | Asn | Asn | His |
|  |  |  | 585 |  |  |  | 590 |  |  |  | 595 |  |  |  |  |

| gtg | atc | gcg | ggc | gcc | acc | gac | atc | aat | gcg | ttc | agc | gtc | ggc | tcc | ggc | 1880 |
| Val | Ile | Ala | Gly | Ala | Thr | Asp | Ile | Asn | Ala | Phe | Ser | Val | Gly | Ser | Gly |
|  |  | 600 |  |  |  | 605 |  |  |  | 610 |  |  |  |  |  |

| caa | acc | tac | ggc | gtc | gat | gtg | gtc | ggg | tat | gac | cgc | acc | cag | gat | gtc | 1928 |
| Gln | Thr | Tyr | Gly | Val | Asp | Val | Val | Gly | Tyr | Asp | Arg | Thr | Gln | Asp | Val |
|  | 615 |  |  |  | 620 |  |  |  | 625 |  |  |  |  |  |  |

| gcg | gtg | ctg | cag | ctg | cgc | ggt | gcc | ggt | ggc | ctg | ccg | tcg | gcg | gcg | atc | 1976 |
| Ala | Val | Leu | Gln | Leu | Arg | Gly | Ala | Gly | Gly | Leu | Pro | Ser | Ala | Ala | Ile |
| 630 |  |  |  | 635 |  |  |  | 640 |  |  |  | 645 |  |  |  |

| ggt | ggc | ggc | gtc | gcg | gtt | ggt | gag | ccc | gtc | gtc | gcg | atg | ggc | aac | agc | 2024 |

```
Gly Gly Gly Val Ala Val Gly Glu Pro Val Ala Met Gly Asn Ser
                650                 655                 660 ggt ggg cag ggc gga acg ccc cgt gcg gtg cct ggc agg gtg gtc gcg    2072
Gly Gly Gln Gly Gly Thr Pro Arg Ala Val Pro Gly Arg Val Val Ala
            665                 670                 675 ctc ggc caa acc gtg cag gcg tcg gat tcg ctg acc ggt gcc gaa gag    2120
Leu Gly Gln Thr Val Gln Ala Ser Asp Ser Leu Thr Gly Ala Glu Glu
            680                 685                 690 aca ttg aac ggg ttg atc cag ttc gat gcc gcg atc cag ccc ggt gat    2168
Thr Leu Asn Gly Leu Ile Gln Phe Asp Ala Ala Ile Gln Pro Gly Asp
        695                 700                 705 tcg ggc ggg ccc gtc gtc aac ggc cta gga cag gtg gtc ggt atg aac    2216
Ser Gly Gly Pro Val Val Asn Gly Leu Gly Gln Val Val Gly Met Asn
710                 715                 720                 725 acg gcc gcg tcc taggatatcc atcacactgg cggccgctcg agcagatccg        2268
Thr Ala Ala Ser gntgtaacaa agcccgaaa                                               2287

<210> SEQ ID NO 2
<211> LENGTH: 729
<212> TYPE: PRT
<213> ORGANISM: Artificial Sequence
<220> FEATURE:
<223> OTHER INFORMATION: Tri-fusion protein Mtb72F (Ral2-TbH9-Ra35 or
      Mtb32-Mtb39)

<400> SEQUENCE: 2

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Arg Met Tyr Ala Gly
145                 150                 155                 160

Pro Gly Ser Ala Ser Leu Val Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240
```

```
Thr Ala Tyr Gly Leu Thr Val Pro Pro Val Ile Ala Glu Asn Arg
            245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
            275                 280                 285

Asp Ala Ala Met Phe Gly Tyr Ala Ala Thr Ala Thr Ala Thr
290                 295                 300

Ala Thr Leu Leu Pro Phe Glu Glu Ala Pro Glu Met Thr Ser Ala Gly
305                 310                 315                 320

Gly Leu Leu Glu Gln Ala Ala Val Glu Glu Ala Ser Asp Thr Ala
            325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
            355                 360                 365

Trp Lys Thr Val Ser Pro His Arg Ser Pro Ile Ser Asn Met Val Ser
            370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
            405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Val Ala Ala
            435                 440                 445

Asn Leu Gly Arg Ala Ala Ser Val Gly Ser Leu Ser Val Pro Gln Ala
            450                 455                 460

Trp Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
            485                 490                 495

Gly Gly Leu Pro Val Gly Met Gly Ala Arg Ala Gly Gly Leu
            500                 505                 510

Ser Gly Val Leu Arg Val Pro Pro Arg Pro Tyr Val Met Pro His Ser
            515                 520                 525

Pro Ala Ala Gly Asp Ile Ala Pro Pro Ala Leu Ser Gln Asp Arg Phe
530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
            565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
            595                 600                 605

Ser Val Gly Ser Gly Gln Thr Tyr Gly Val Asp Val Val Gly Tyr Asp
            610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
            645                 650                 655
```

Ala Met Gly Asn Ser Gly Gly Gln Gly Gly Thr Pro Arg Ala Val Pro
                660                 665                 670

Gly Arg Val Val Ala Leu Gly Gln Thr Val Gln Ala Ser Asp Ser Leu
            675                 680                 685

Thr Gly Ala Glu Glu Thr Leu Asn Gly Leu Ile Gln Phe Asp Ala Ala
        690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser
                725

<210> SEQ ID NO 3
<211> LENGTH: 2178
<212> TYPE: DNA
<213> ORGANISM: Artificial Sequence
<220> FEATURE:
<223> OTHER INFORMATION: Variant of tri-fusion protein Mtb72F
      (Ra12-TbH9-Ra35 or Mtb32-Mtb39)
<220> FEATURE:
<221> NAME/KEY: misc_feature
<222> LOCATION: (4)...(9)
<223> OTHER INFORMATION: 'cat cac' instead of 'cat cac cat cac cat cac'
<220> FEATURE:
<221> NAME/KEY: misc_feature
<222> LOCATION: (2116)...(2118)
<223> OTHER INFORMATION: 'gcg' instead of 'tcg'

<400> SEQUENCE: 3

```
atgcatcaca cggccgcgtc cgataacttc cagctgtccc agggtgggca gggattcgcc      60
attccgatcg ggcaggcgat ggcgatcgcg ggccagatcc gatcgggtgg ggggtcaccc     120
accgttcata tcgggcctac cgccttcctc ggcttgggtg ttgtcgacaa caacggcaac     180
ggcgcacgag tccaacgcgt ggtcgggagc gctccggcgg caagtctcgg catctccacc     240
ggcgacgtga tcaccgcggt cgacggcgct ccgatcaact cggccaccgc gatggcggac     300
gcgcttaacg ggcatcatcc cggtgacgtc atctcggtga cctggcaaac caagtcgggc     360
ggcacgcgta cagggaacgt gacattggcc gagggacccc cggccgaatt catggtggat     420
ttcggggcgt taccaccgga gatcaactcc gcgaggatgt acgccggccc gggttcggcc     480
tcgctggtgg ccgcggctca gatgtgggac agcgtggcga gtgacctgtt tcggccgcg      540
tcggcgtttc agtcggtggt ctgggtctct acggtggggt cgtggatagg ttcgtcggcg     600
ggtctgatgg tggcggcggc ctcgccgtat gtggcgtgga tgagcgtcac cgcggggcag     660
gccgagctga ccgccgccca ggtccgggtt gctgcggcgg cctacgagac ggcgtatggg     720
ctgacggtgc ccccgccggt gatcgccgag aaccgtgctg aactgatgat tctgatagcg     780
accaacctct gggggcaaaaa caccccggcg atcgcggtca acgaggccga atacggcgag     840
atgtgggccc aagacgccgc cgcgatgttt ggctacgccg cggcgacggc gacggcgacg     900
gcgacgttgc tgccgttcga ggaggcgccg gagatgacca gcgcgggtgg gctcctcgag     960
caggccgccg cggtcgagga ggcctccgac accgccgcgg cgaaccagtt gatgaacaat    1020
gtgccccagg cgctgcaaca gctggcccag cccacgcagg gcaccacgcc ttcttccaag    1080
ctgggtggcc tgtggaagac ggtctcgccg catcggtcgc cgatcagcaa catggtgtcg    1140
atggccaaca accacatgtc gatgaccaac tcgggtgtgt cgatgaccaa caccttgagc    1200
tcgatgttga ggggctttgc tccggcggcg gccgccaggg ccgtgcaaac cgcggcgcaa    1260
aacgggtcc gggcgatgag ctcgctgggc agctcgctgg ttcttcggg tctggcggt    1320
ggggtggccg ccaacttggg tcgggcggcc tcggtcggtt cgttgtcggt gccgcaggcc    1380
```

-continued

```
tgggccgcgg ccaaccaggc agtcaccccg gcggcgcggg cgctgccgct gaccagcctg    1440
accagcgccg cggaaagagg gcccgggcag atgctgggcg gctgccggt  ggggcagatg    1500 ggcgccaggg ccggtggtgg gctcagtggt gtgctgcgtg ttccgccgcg accctatgtg    1560
atgccgcatt ctccggcagc cggcgatatc gccccgccgg ccttgtcgca ggaccggttc    1620
gccgacttcc ccgcgctgcc cctcgacccg tccgcgatgg tcgcccaagt ggggccacag    1680
gtggtcaaca tcaacaccaa actgggctac aacaacgccg tgggcgccgg gaccggcatc    1740
gtcatcgatc ccaacggtgt cgtgctgacc aacaaccacg tgatcgcggg cgccaccgac    1800
atcaatgcgt tcagcgtcgg ctccggccaa acctacggcg tcgatgtggt cgggtatgac    1860
cgcacccagg atgtcgcggt gctgcagctg cgcggtgccg gtggcctgcc gtcggcggcg    1920
atcggtggcg gcgtcgcggt tggtgagccc gtcgtcgcga tgggcaacag cggtgggcag    1980
ggcggaacgc cccgtgcggt gcctggcagg gtggtcgcgc tcggccaaac cgtgcaggcg    2040
tcggattcgc tgaccggtgc cgaagagaca ttgaacgggt tgatccagtt cgatgccgcg    2100
atccagcccg gtgatgcggg cgggcccgtc gtcaacggcc taggacaggt ggtcggtatg    2160
aacacggccg cgtcctag                                                  2178
```

<210> SEQ ID NO 4
<211> LENGTH: 725
<212> TYPE: PRT
<213> ORGANISM: Artificial Sequence
<220> FEATURE:
<223> OTHER INFORMATION: Variant of tri-fusion protein Mtb72F
      (Ra12-TbH9-Ra35 or Mtb32-Mtb39)
<220> FEATURE:
<221> NAME/KEY: misc_feature
<222> LOCATION: (2)...(3)
<223> OTHER INFORMATION: 'His His' instead of 'His His His His His His'
<220> FEATURE:
<221> NAME/KEY: misc_feature
<222> LOCATION: (706)...(706)
<223> OTHER INFORMATION: 'Ala' instead of 'Ser'

<400> SEQUENCE: 4

```
Met His His Thr Ala Ala Ser Asp Asn Phe Gln Leu Ser Gln Gly Gly
  1               5                  10                  15

Gln Gly Phe Ala Ile Pro Ile Gly Gln Ala Met Ala Ile Ala Gly Gln
                 20                  25                  30

Ile Arg Ser Gly Gly Gly Ser Pro Thr Val His Ile Gly Pro Thr Ala
             35                  40                  45

Phe Leu Gly Leu Gly Val Val Asp Asn Asn Gly Asn Gly Ala Arg Val
         50                  55                  60

Gln Arg Val Val Gly Ser Ala Pro Ala Ala Ser Leu Gly Ile Ser Thr
 65                  70                  75                  80

Gly Asp Val Ile Thr Ala Val Asp Gly Ala Pro Ile Asn Ser Ala Thr
                 85                  90                  95

Ala Met Ala Asp Ala Leu Asn Gly His His Pro Gly Asp Val Ile Ser
                100                 105                 110

Val Thr Trp Gln Thr Lys Ser Gly Gly Thr Arg Thr Gly Asn Val Thr
            115                 120                 125

Leu Ala Glu Gly Pro Pro Ala Glu Phe Met Val Asp Phe Gly Ala Leu
        130                 135                 140

Pro Pro Glu Ile Asn Ser Ala Arg Met Tyr Ala Gly Pro Gly Ser Ala
145                 150                 155                 160

Ser Leu Val Ala Ala Ala Gln Met Trp Asp Ser Val Ala Ser Asp Leu
```

```
                165                 170                 175
Phe Ser Ala Ala Ser Ala Phe Gln Ser Val Val Trp Gly Leu Thr Val
            180                 185                 190
Gly Ser Trp Ile Gly Ser Ser Ala Gly Leu Met Val Ala Ala Ala Ser
            195                 200                 205
Pro Tyr Val Ala Trp Met Ser Val Thr Ala Gly Gln Ala Glu Leu Thr
            210                 215                 220
Ala Ala Gln Val Arg Val Ala Ala Ala Tyr Glu Thr Ala Tyr Gly
225                 230                 235                 240
Leu Thr Val Pro Pro Pro Val Ile Ala Glu Asn Arg Ala Glu Leu Met
                245                 250                 255
Ile Leu Ile Ala Thr Asn Leu Leu Gly Gln Asn Thr Pro Ala Ile Ala
            260                 265                 270
Val Asn Glu Ala Glu Tyr Gly Glu Met Trp Ala Gln Asp Ala Ala
            275                 280                 285
Met Phe Gly Tyr Ala Ala Ala Thr Ala Thr Ala Thr Ala Thr Leu Leu
            290                 295                 300
Pro Phe Glu Glu Ala Pro Glu Met Thr Ser Ala Gly Gly Leu Leu Glu
305                 310                 315                 320
Gln Ala Ala Ala Val Glu Glu Ala Ser Asp Thr Ala Ala Ala Asn Gln
                325                 330                 335
Leu Met Asn Asn Val Pro Gln Ala Leu Gln Gln Leu Ala Gln Pro Thr
            340                 345                 350
Gln Gly Thr Thr Pro Ser Ser Lys Leu Gly Gly Leu Trp Lys Thr Val
            355                 360                 365
Ser Pro His Arg Ser Pro Ile Ser Asn Met Val Ser Met Ala Asn Asn
            370                 375                 380
His Met Ser Met Thr Asn Ser Gly Val Ser Met Thr Asn Thr Leu Ser
385                 390                 395                 400
Ser Met Leu Lys Gly Phe Ala Pro Ala Ala Ala Ala Gln Ala Val Gln
                405                 410                 415
Thr Ala Ala Gln Asn Gly Val Arg Ala Met Ser Ser Leu Gly Ser Ser
            420                 425                 430
Leu Gly Ser Ser Gly Leu Gly Gly Val Ala Ala Asn Leu Gly Arg
            435                 440                 445
Ala Ala Ser Val Gly Ser Leu Ser Val Pro Gln Ala Trp Ala Ala Ala
            450                 455                 460
Asn Gln Ala Val Thr Pro Ala Ala Arg Ala Leu Pro Leu Thr Ser Leu
465                 470                 475                 480
Thr Ser Ala Ala Glu Arg Gly Pro Gly Gln Met Leu Gly Gly Leu Pro
                485                 490                 495
Val Gly Gln Met Gly Ala Arg Ala Gly Gly Leu Ser Gly Val Leu
            500                 505                 510
Arg Val Pro Pro Arg Pro Tyr Val Met Pro His Ser Pro Ala Ala Gly
            515                 520                 525
Asp Ile Ala Pro Pro Ala Leu Ser Gln Asp Arg Phe Ala Asp Phe Pro
            530                 535                 540
Ala Leu Pro Leu Asp Pro Ser Ala Met Val Ala Gln Val Gly Pro Gln
545                 550                 555                 560
Val Val Asn Ile Asn Thr Lys Leu Gly Tyr Asn Asn Ala Val Gly Ala
                565                 570                 575
Gly Thr Gly Ile Val Ile Asp Pro Asn Gly Val Val Leu Thr Asn Asn
            580                 585                 590
```

His Val Ile Ala Gly Ala Thr Asp Ile Asn Ala Phe Ser Val Gly Ser
    595                 600                 605

Gly Gln Thr Tyr Gly Val Asp Val Val Gly Tyr Asp Arg Thr Gln Asp
610                 615                 620

Val Ala Val Leu Gln Leu Arg Gly Ala Gly Leu Pro Ser Ala Ala
625                 630                 635                 640

Ile Gly Gly Val Ala Val Gly Glu Pro Val Ala Met Gly Asn
                    645                 650                 655

Ser Gly Gly Gln Gly Gly Thr Pro Arg Ala Val Pro Gly Arg Val Val
            660                 665                 670

Ala Leu Gly Gln Thr Val Gln Ala Ser Asp Ser Leu Thr Gly Ala Glu
            675                 680                 685

Glu Thr Leu Asn Gly Leu Ile Gln Phe Asp Ala Ala Ile Gln Pro Gly
        690                 695                 700

Asp Ala Gly Gly Pro Val Val Asn Gly Leu Gly Gln Val Val Gly Met
705                 710                 715                 720

Asn Thr Ala Ala Ser
            725

<210> SEQ ID NO 5
<211> LENGTH: 2172
<212> TYPE: DNA
<213> ORGANISM: Artificial Sequence
<220> FEATURE:
<223> OTHER INFORMATION: Mtb72F-IND
<220> FEATURE:
<221> NAME/KEY: misc_feature
<222> LOCATION: (4)...(4)
<223> OTHER INFORMATION: Deletion of 'cat cac cat cac cat cac' tag

<400> SEQUENCE: 5

```
atgacggccg cgtccgataa cttccagctg tcccagggtg ggcagggatt cgccattccg      60
atcgggcagg cgatggcgat cgcgggccag atccgatcgg gtgggggtc acccaccgtt     120
catatcgggc ctaccgcctt cctcggcttg ggtgttgtcg acaacaacgg caacggcgca     180
cgagtccaac gcgtggtcgg gagcgctccg gcggcaagtc tcggcatctc caccggcgac     240
gtgatcaccg cggtcgacgg cgctccgatc aactcggcca ccgcgatggc ggacgcgctt     300
aacgggcatc atcccggtga cgtcatctcg gtgacctggc aaaccaagtc gggcggcacg     360
cgtacaggga acgtgacatt ggccgaggga ccccggccg aattcatggt ggatttcggg     420
gcgttaccac cggagatcaa ctccgcgagg atgtacgccg gccgggttc ggcctcgctg     480
gtggccgcgg ctcagatgtg ggacagcgtg gcgagtgacc tgttttcggc cgcgtcggcg     540
tttcagtcgg tggtctgggg tctgacggtg gggtcgtgga taggttcgtc ggcgggtctg     600
atggtggcgg cggcctcgcc gtatgtggcg tggatgagcg tcaccgcggg gcaggccgag     660
ctgaccgccg cccaggtccg ggttgctgcg gcggcctacg agacggcgta tgggctgacg     720
gtgccccgc cggtgatcgc cgagaaccgt gctgaactga tgattctgat agcgaccaac     780
ctcttggggc aaaacacccc ggcgatcgcg gtcaacgagg ccgaatacgg cgagatgtgg     840
gcccaagacg ccgccgcgat gtttggctac gccgcggcga cggcgacggc gacggcgacg     900
ttgctgccgt tcgaggaggc gccggagatg accagcgcgg gtgggctcct cgagcaggcc     960
gccgcggtcg aggaggcctc cgacaccgcc gcggcgaacc agttgatgaa caatgtgccc    1020
caggcgctgc aacagctggc ccagcccacg cagggcacca cgccttcttc caagctgggt    1080
ggcctgtgga agacggtctc gccgcatcgg tcgccgatca gcaacatggt gtcgatggcc    1140
```

```
aacaaccaca tgtcgatgac caactcgggt gtgtcgatga ccaacacctt gagctcgatg    1200
ttgaagggct ttgctccggc ggcggccgcc caggccgtgc aaaccgcggc gcaaaacggg    1260
gtccgggcga tgagctcgct gggcagctcg ctgggttctt cgggtctggg cggtggggtg    1320
gccgccaact tgggtcgggc ggcctcggtc ggttcgttgt cggtgccgca ggcctgggcc    1380
gcggccaacc aggcagtcac cccggcggcg cgggcgctgc cgctgaccag cctgaccagc    1440
gccgcggaaa gagggcccgg gcagatgctg gcgggctgc cggtggggca gatgggcgcc    1500
agggccggtg gtgggctcag tggtgtgctg cgtgttccgc cgcgacccta tgtgatgccg    1560
cattctccgg cagccggcga tatcgccccg ccggccttgt cgcaggaccg gttcgccgac    1620
ttccccgcgc tgccctcga cccgtccgcg atggtcgccc aagtggggcc acaggtggtc    1680
aacatcaaca ccaaactggg ctacaacaac gccgtgggcg ccgggaccgg catcgtcatc    1740
gatcccaacg gtgtcgtgct gaccaacaac cacgtgatcg cgggcgccac cgacatcaat    1800
gcgttcagcg tcggctccgg ccaaacctac ggcgtcgatg tggtcgggta tgaccgcacc    1860
caggatgtcg cggtgctgca gctgcgcggt gccggtggcc tgccgtcggc ggcgatcggt    1920
ggcggcgtcg cggttggtga ccccgtcgtc gcgatgggca acagcggtgg gcagggcgga    1980
acgccccgtg cggtgcctgg cagggtggtc gcgctcggcc aaaccgtgca ggcgtcggat    2040
tcgctgaccg gtgccgaaga gacattgaac gggttgatcc agttcgatgc cgcgatccag    2100
cccggtgatt cgggcgggcc cgtcgtcaac ggcctaggac aggtggtcgg tatgaacacg    2160
gccgcgtcct ga                                                       2172
```

<210> SEQ ID NO 6
<211> LENGTH: 723
<212> TYPE: PRT
<213> ORGANISM: Artificial Sequence
<220> FEATURE:
<223> OTHER INFORMATION: Mtb72F-IND
<220> FEATURE:
<221> NAME/KEY: misc_feature
<222> LOCATION: (2)...(2)
<223> OTHER INFORMATION: Deletion of 'His His His His His His' tag

<400> SEQUENCE: 6

```
Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
```

```
            145                 150                 155                 160
Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
                180                 185                 190

Trp Ile Gly Ser Ser Ala Gly Leu Met Val Ala Ala Ser Pro Tyr
                195                 200                 205

Val Ala Trp Met Ser Val Thr Ala Gly Gln Ala Glu Leu Thr Ala Ala
            210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                    245                 250                 255

Ile Ala Thr Asn Leu Leu Gly Gln Asn Thr Pro Ala Ile Ala Val Asn
                260                 265                 270

Glu Ala Glu Tyr Gly Glu Met Trp Ala Gln Asp Ala Ala Ala Met Phe
                275                 280                 285

Gly Tyr Ala Ala Ala Thr Ala Thr Ala Thr Ala Thr Leu Leu Pro Phe
            290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Asn Gln Leu Met
                325                 330                 335

Asn Asn Val Pro Gln Ala Leu Gln Gln Leu Ala Gln Pro Thr Gln Gly
                340                 345                 350

Thr Thr Pro Ser Ser Lys Leu Gly Gly Leu Trp Lys Thr Val Ser Pro
            355                 360                 365

His Arg Ser Pro Ile Ser Asn Met Val Ser Met Ala Asn Asn His Met
            370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
                420                 425                 430

Ser Ser Gly Leu Gly Gly Val Ala Ala Asn Leu Gly Arg Ala Ala
                435                 440                 445

Ser Val Gly Ser Leu Ser Val Pro Gln Ala Trp Ala Ala Ala Asn Gln
            450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Leu Ser Gly Val Leu Arg Val
                500                 505                 510

Pro Pro Arg Pro Tyr Val Met Pro His Ser Pro Ala Ala Gly Asp Ile
            515                 520                 525

Ala Pro Pro Ala Leu Ser Gln Asp Arg Phe Ala Asp Phe Pro Ala Leu
                530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575
```

```
Gly Ile Val Ile Asp Pro Asn Gly Val Val Leu Thr Asn Asn His Val
                580                 585                 590

Ile Ala Gly Ala Thr Asp Ile Asn Ala Phe Ser Val Gly Ser Gly Gln
            595                 600                 605

Thr Tyr Gly Val Asp Val Val Gly Tyr Asp Arg Thr Gln Asp Val Ala
        610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
        675                 680                 685

Leu Asn Gly Leu Ile Gln Phe Asp Ala Ala Ile Gln Pro Gly Asp Ser
    690                 695                 700

Gly Gly Pro Val Val Asn Gly Leu Gly Gln Val Val Gly Met Asn Thr
705                 710                 715                 720

Ala Ala Ser

<210> SEQ ID NO 7
<211> LENGTH: 51
<212> TYPE: DNA
<213> ORGANISM: Artificial Sequence
<220> FEATURE:
<223> OTHER INFORMATION: Oligonucleotide of a C-terminal portion of
      Mtb32

<400> SEQUENCE: 7
caattacata tgcatcacca tcaccatcac acggccgcgt ccgataactt c            51

<210> SEQ ID NO 8
<211> LENGTH: 33
<212> TYPE: DNA
<213> ORGANISM: Artificial Sequence
<220> FEATURE:
<223> OTHER INFORMATION: Oligonucleotide of a C-terminal portion of
      Mtb32

<400> SEQUENCE: 8
ctaatcgaat ccggccgggg gtccctcggc caa                                33

<210> SEQ ID NO 9
<211> LENGTH: 33
<212> TYPE: DNA
<213> ORGANISM: Artificial Sequence
<220> FEATURE:
<223> OTHER INFORMATION: Oligonucleotide of a portion of Mtb39

<400> SEQUENCE: 9
ctaatcgaat tcatggtgga tttcggggcg tta                                33

<210> SEQ ID NO 10
<211> LENGTH: 33
<212> TYPE: DNA
<213> ORGANISM: Artificial Sequence
<220> FEATURE:
<223> OTHER INFORMATION: Oligonucleotide of a portion of Mtb39

<400> SEQUENCE: 10
ctaatcgata tcgccggctg ccggagaatg cgg                                33
```

```
<210> SEQ ID NO 11
<211> LENGTH: 36
<212> TYPE: DNA
<213> ORGANISM: Artificial Sequence
<220> FEATURE:
<223> OTHER INFORMATION: Oligonucleotide of an N-terminal portion of
      Mtb32

<400> SEQUENCE: 11
ctaatcgata tcgcccgcc ggccttgtcg caggac                                  36

<210> SEQ ID NO 12
<211> LENGTH: 35
<212> TYPE: DNA
<213> ORGANISM: Artificial Sequence
<220> FEATURE:
<223> OTHER INFORMATION: Oligonucleotide of an N-terminal portion of
      Mtb32

<400> SEQUENCE: 12
ctaatcgata tcctaggacg cggccgtgtt catac                                  35
```